US008881732B2

(12) United States Patent
Blurton et al.

(10) Patent No.: US 8,881,732 B2
(45) Date of Patent: Nov. 11, 2014

(54) METHOD AND APPARATUS FOR RETENTION OF ADIPOSE TISSUE

(71) Applicant: Plexus Biomedical, Inc., Oakland, TN (US)

(72) Inventors: David D. Blurton, Whiteville, TN (US); Mark Buchanan, Atoka, TN (US)

(*) Notice: Subject to any disclaimer, the term of this patent is extended or adjusted under 35 U.S.C. 154(b) by 103 days.

(21) Appl. No.: 13/727,145

(22) Filed: Dec. 26, 2012

(65) Prior Publication Data

US 2013/0186410 A1 Jul. 25, 2013

Related U.S. Application Data

(62) Division of application No. 12/106,821, filed on Apr. 21, 2008, now abandoned.

(51) Int. Cl.
*A61G 15/00* (2006.01)

(52) U.S. Cl.
USPC .......................................................... 128/845

(58) Field of Classification Search
USPC .............................. 128/845, 846; 602/41–54
See application file for complete search history.

(56) References Cited

U.S. PATENT DOCUMENTS

| | | | |
|---|---|---|---|
| 572,465 A | 12/1896 | Woolfolk et al. |
| 811,167 A | 1/1906 | Paddock |
| 933,610 A | 9/1909 | Yanowsky |
| 1,529,937 A | 3/1925 | Turcotte |
| 1,565,808 A | 12/1925 | Levy |
| 1,983,636 A | 12/1934 | Palkens |
| 2,104,699 A | 1/1938 | O'Dell |
| 2,282,021 A | 5/1942 | Benningfield |
| 2,327,671 A | 8/1943 | Rupprecht |
| 2,719,568 A | 10/1955 | Webb |
| 2,840,822 A | 7/1958 | Ericsson |
| 3,101,718 A | 8/1963 | Rocker |
| 3,103,316 A | 9/1963 | Schaal |
| 3,116,735 A | 1/1964 | Geimer |
| 3,452,362 A | 7/1969 | Korolick et al. |
| 3,554,190 A | 1/1971 | Kaplan |
| 4,239,037 A | 12/1980 | Fausone |
| 4,530,122 A | 7/1985 | Sanders et al. |

(Continued)

FOREIGN PATENT DOCUMENTS

| | | |
|---|---|---|
| EP | 1 477 197 A1 | 11/2004 |
| RU | 2 196 491 C1 | 1/2003 |

(Continued)

OTHER PUBLICATIONS

U.S. Appl. No. 60/744,017, filed Mar. 31, 2006, Sharp.

(Continued)

*Primary Examiner* — Michael A. Brown
(74) *Attorney, Agent, or Firm* — Haynes and Boone, LLP

(57) ABSTRACT

A tissue retention system to assist in maintaining adipose tissue on a patient in a displaced position during a medical procedure to provide access to a body region of the patient includes a flexible anchor pad having a pad length and a pad width. The anchor pad may include a pad body with an adhesive surface thereon, the adhesive being configured to selectively adhere to a patient's skin. The anchor pad also may include an opposing first attachment surface facing away from the adhesive surface. The tissue retention system also may include a flexible tension member having a second attachment surface.

20 Claims, 14 Drawing Sheets

(56) References Cited

U.S. PATENT DOCUMENTS

| | | | |
|---|---|---|---|
| 4,615,334 A * | 10/1986 | Jaeger | 600/195 |
| 4,691,333 A | 9/1987 | Gabriele et al. | |
| 4,706,661 A | 11/1987 | Barrett | |
| 4,732,146 A | 3/1988 | Fasline et al. | |
| 4,782,535 A | 11/1988 | Yewer, Jr. et al. | |
| 4,822,317 A | 4/1989 | Wimmer | |
| 4,825,866 A | 5/1989 | Pierce | |
| 4,866,789 A | 9/1989 | Dorm | |
| 4,981,307 A | 1/1991 | Walsh | |
| 4,995,383 A | 2/1991 | Anderson | |
| 5,007,412 A | 4/1991 | DeWall | |
| 5,040,524 A | 8/1991 | Votel et al. | |
| 5,148,549 A | 9/1992 | Sydor | |
| 5,234,462 A | 8/1993 | Pavletic | |
| 5,432,951 A | 7/1995 | Yewer, Jr. | |
| 5,493,735 A | 2/1996 | Rice | |
| 5,569,165 A | 10/1996 | Chin et al. | |
| 5,690,607 A | 11/1997 | Chin et al. | |
| 5,709,650 A | 1/1998 | Colman | |
| 5,843,025 A | 12/1998 | Shaari | |
| 5,928,059 A | 7/1999 | Wicks | |
| 5,991,979 A | 11/1999 | Moore et al. | |
| 6,071,175 A | 6/2000 | Working, III | |
| 6,123,667 A | 9/2000 | Poff et al. | |
| 6,146,345 A | 11/2000 | Mignard | |
| 6,159,070 A | 12/2000 | Schwartz et al. | |
| 6,572,541 B1 | 6/2003 | Petersvik | |
| 6,623,588 B1 | 9/2003 | Rasmussen | |
| 6,710,099 B2 | 3/2004 | Cinelli et al. | |
| 7,198,609 B2 | 4/2007 | Rolnick | |
| 2003/0092969 A1 | 5/2003 | O'Malley et al. | |
| 2004/0067716 A1 | 4/2004 | Wakefield | |
| 2004/0088031 A1 | 5/2004 | Gomez | |
| 2004/0186356 A1 | 9/2004 | O'Malley et al. | |
| 2005/0203565 A1 | 9/2005 | Retty et al. | |
| 2006/0149177 A1 | 7/2006 | Root et al. | |
| 2006/0180158 A1 | 8/2006 | McKnight et al. | |
| 2007/0021779 A1 * | 1/2007 | Garvin et al. | 606/216 |
| 2007/0232864 A1 | 10/2007 | Sharp et al. | |
| 2011/0275983 A1 * | 11/2011 | Quisenberry et al. | 604/23 |

FOREIGN PATENT DOCUMENTS

| | | |
|---|---|---|
| WO | WO 9629013 | 9/1996 |
| WO | WO 9932003 | 7/1999 |
| WO | WO 2006086785 A2 | 8/2006 |
| WO | WO 2007114982 A1 | 10/2007 |

OTHER PUBLICATIONS

Bryant Ruth A., "Saving the Skin From Tape Injuries", Reprinted from American Journal of Nursing, Feb. 1988, vol. 88, No. 2, 3 pages.

Dykes et al., "Effects of Adhesive Dressings on the Stratum Corneum of the Skin", Journal of Wound Care, February, vol. 10, No. 2 2001, pp. 1-4.

Gerhardt, et al., "Study of Skin-Fabric Interactions of Relevance to Decubitus: Friction and Contact-Pressure Measurements", Skin Research and Technology, 2008, 14, pp. 77-88, printed in Singapore.

Goossens, et al., "Decubitus Risk: Is Shear More Important Than Pressure?", Proceedings of the 1EA 2000/HFES 2000 Congress, pp. 4-700-4-703.

Jacquet et al., "A New Experimental Method for Measuring Skin's Natural Tension", Skin Research and Technology 2008; 14: pp. 1-7, printed in Singapore.

Karwoski et al., "Experiments on Peeling Adhesive Tapes from Human Forearms", Skin Research and Technology 2004; 10: pp. 271-277, printed in Denmark.

Koval et al., "Tape Blisters Following Hip Surgery", A Prospective, Randomized Study of Two Types of Tape, Investigation performed at The Hospital for Joint Diseases, New York, and Jamaica Hospital Medical Center, Jamaica, New York, pp. 1884-1887, The Journal of Bone and Joint Surgery, Inc.

Lippmann et al., "An Alternative Anesthetic Technique for the Morbidly Obese Patient Undergoing Endovascular Repair of an Abdominal Aortic Aneurysm", From the Departments of Anesthesiology and Surgery, Harbor-UCLA Medical Center, Torrance, CA, Anesth Analg 2003;97, pp. 981-983.

Murahata, et al., "Preliminary Studies on the Relationship Among Peel Force, Quantitative Measures of Skin Damage and Subjective Discomfort", Skin Research and Technology 2008; 14: pp. 1-6, printed in Singapore.

Ohura et al., "Influence of External Forces (Pressure and Shear Force) on Superficial Layer and Subcutis of Porcine Skin and Effects of Dressing Materials: Are Dressing Materials Beneficial for Reducing Pressure and Shear Force in Tissues?", Wound Repair and Regeneration (2008); 16, pp. 102-107.

3M Health Care 2005, "Reducing the Risk of Superficial Damage Related to Adhesive Use", 2 pages.

Loerakker, Sandra, "Aetiology of Pressure Ulcers", Eindhoven University of Technology, Dept. of Biomedical Engineering, Section Materials Technology, Div. Biomechanics and Tissue Engineering, Oct. 2007, 31 pages.

Murahata, et. al., "Preliminary Studies on the Relationship Among Peel Force, Quantitative Measures of Skin Damage and Subjective Discomfort", Skin Research and Technology 2008; 14: pp. 1-6, printed in Singapore.

Ohura et al., "Influence of External Forces (Pressure and Shear Force) on Superficial Layer and Subcutis of Porcine Skin and Effects of Dressing Materials: Are Dressing Materials Beneficial for Reducing Pressure and Shear Force in Tissues?", Wound Repair and Regeneration (2008), 16, pp. 102-107.

Sarifakioglu et al., "Dressing Spray Enhances the Adhesive Strength of Surgical Dressing Tapes", Indian Journal of Dermatology, Venereology and Leprology, printed from www.ijdvl.com/article. asp?issn=0378-6323;year=2006;volume=72;issue=5;spage=353;epage=356, on Apr. 16, 2008, pp. 1-5.

Thomas Steve, "World Wide Wounds—Atraumatic Dressings", Published Jan. 2003, printed from www.worldwidewounds.com/2003/january/Thomas/Atraumatic-Dressings.html on Jan. 22, 2009, pp. 1-10.

Viegas et al., "Preventing a Surgical Complication During Cesarean Delivery in a Morbidly Obese Patient: A Simple Apparatus to Retract the Abdominal Panniculus", MedGenMed Ob/Gyn & Women's Health, Medscape General Medicine, 2006;8(1):52 printed from www.medscape.com/viewarticle/518147_print, on Nov. 16, 2007, pp. 1-5.

Wang et al., "In Vivo Biomechanics of the Fingerpad Skin Under Local Tangential Traction", Journal of Biomechanics, 2007, 40(4):851-860.

Breast Forms printed from www.geocities.com/KarenSpecial/bustform.html on Jan. 9, 2008, pp. 1-11.

Canica, Dynamic Wound Stabilization, "SutureSafe" printed from www.canica.com/suturesafe.asp on Feb. 14, 2008, 2 pages.

Max-Support Abdominal Retraction Belt by Vascular Solutions, Brochure, pp. 1-4.

FLEXcon Providing Solutions in Pressure Sensitive Films, Product Construction Sheet, 1 page.

3M Preliminary Technical Information Sheet, 3M Gamma Stable Medical Fastener, #7333, Gamma Stable Hook Fastener with Adhesive, 2 pages.

3M Preliminary Technical Information Sheet, 3M Gamma Stable Medical Fastener, #7331, Gamma Stable Loop Fastener with Adhesive, 2 pages.

3M Health Care 2005, "Reducing the Risk of Superficial Skin Damage Related to Adhesive Use", 2 pages.

Vascular Solutions Bringing Solutions to Vascular Medicine, "Max-Support Abdominal Retraction Belt", printed from www.vascularsolutions.com/products/max-support on Jan. 2, 2008, 1 page.

* cited by examiner

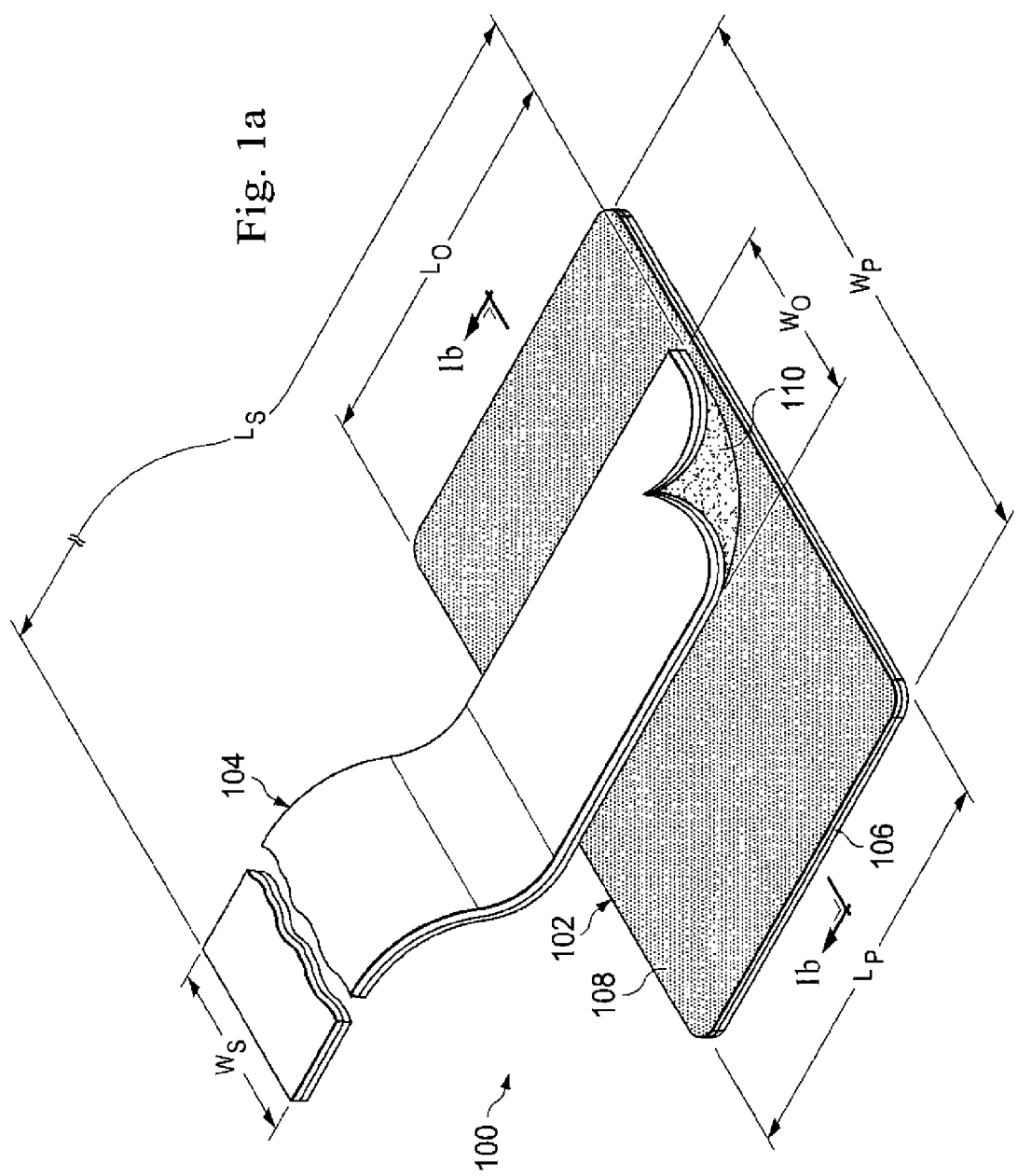

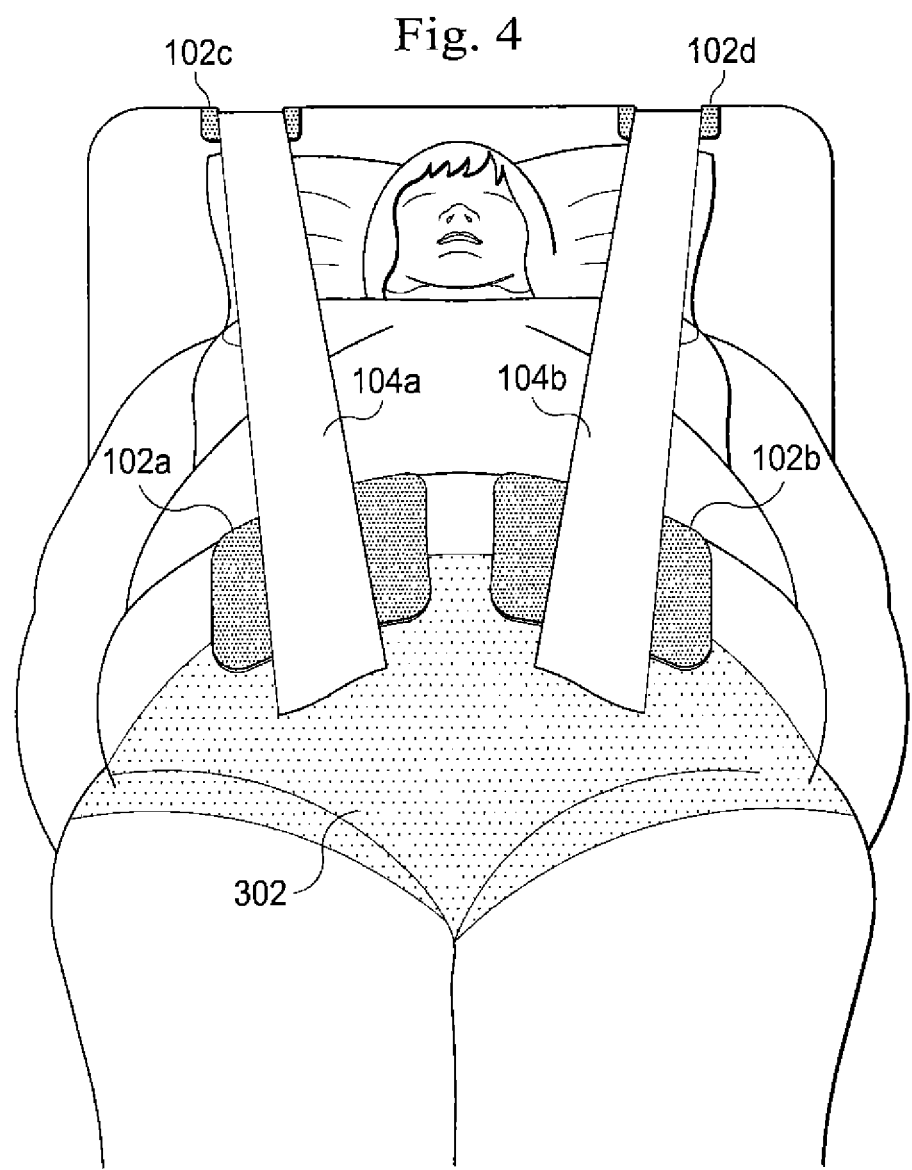

METHOD AND APPARATUS FOR RETENTION OF ADIPOSE TISSUE

This application is a divisional of U.S. patent application Ser. No. 12/106,821, filed Apr. 21, 2008, which is incorporated herein by reference in its entirety.

TECHNICAL FIELD

This disclosure relates in general to a method and system for retention of tissue in a variety of applications and retaining objects in relation to tissue. More particularly, in some particular embodiments this disclosure relates to methods and systems for retention of adipose tissue and maintaining it in a displaced position during a medical procedure on a patient.

BACKGROUND

The size and constitution of the human body can affect the availability and efficiency of medical care that can be provided. For example, adipose tissue, such as a pannus or an abdominal apron on an obese patient, may completely obscure access to a body region requiring a medical procedure. In cases of excessive adipose tissue, a treating medical professional attempting to examine, treat or otherwise access the lower abdomen or groin region of the patient may have only limited visualization and may have insufficient access to perform procedures.

Current systems and methods for dealing with adipose tissue, such as the pannus, are inadequate. These may include having medical staff use their hands to hold the weight of the pannus or other adipose body tissue during the entire procedure, may include using tape (or tape in conjunction with spray adhesives) to hold the pannus or other adipose tissue, may include using hooks that secure or grab the pannus or other adipose tissue, and may include supporting the pannus or adipose tissue with a sheet that may be tied around the patient's abdomen and to a bed side rail or chair. These all have shortcomings that continue to make medical procedures difficult.

The present disclosure overcomes one or more shortcomings in the art.

SUMMARY

In one exemplary aspect, the present disclosure is directed to a tissue retention system to assist in maintaining adipose tissue on a patient in a displaced position during a medical procedure to provide access to a body region of the patient. The tissue retention system comprises a flexible anchor pad having an anchor pad width and an anchor pad length. The anchor pad also has an anchor pad area defined at least partially by the width and length. The anchor pad comprises a pad body with an adhesive surface thereon, the adhesive being configured to selectively adhere to a patient's skin. It also comprises an opposing first attachment surface facing away from the adhesive surface. In one embodiment, the first attachment surface includes one of a hook and loop portion of a hook and loop fastener. The tissue retention system also comprises a flexible tension member having a distal portion and a proximal portion. The flexible tension member has a second attachment surface disposed adjacent the distal portion. In some embodiments, the second attachment surface includes the other of the hook and loop portion of a hook and loop fastener. In one embodiment, the tension member has a tension member width less than the anchor pad width and less than the anchor pad length. The flexible tension member is sized to cooperate with the anchor pad to define an overlap area less than the size of the anchor pad area such that loading onto the anchor pad from the tension member is distributed over an area of the skin greater than the area of the overlap of the first and second attachment surfaces.

In another exemplary aspect, the tissue retention system includes a flexible anchor pad having a first attachment surface including one of a hook and loop portion of a hook and loop fastener. The system also includes a flexible tension member having a second attachment surface including the other of the hook and loop portion of a hook and loop fastener. The hook and loop fastener of the first and second attachment surfaces having a 135 degree closure peel strength within the range of about 1-10 oz/inch width.

In another exemplary aspect, the tissue retention system includes a flexible anchor pad and a flexible tension member wherein the flexible tension member has elongation properties and the adhesive of the anchor member has adhesive properties when attached to a patient's skin, such that when the first and second attachment surfaces are fastened, the tension member elongates under tension loads before the adhesive on the anchor pad damages the patient's skin.

In another exemplary aspect, the present disclosure is directed to a kit for maintaining adipose tissue on a patient in a displaced position during a medical procedure to provide access to a body region of the patient. In one embodiment, the includes the tissue retention system. In some embodiments, the kit includes a plurality of flexible anchor pads and at least one flexible tension member.

In another exemplary aspect, the present disclosure is directed to a method of maintaining adipose tissue on a patient in a displaced position during a medical procedure to provide access to a body portion of the patient with a tissue retention system. The method includes adhesively adhering directly to a patient's skin adjacent the adipose tissue an adhesive surface of an anchor pad, the anchor pad having a pad length and a pad width, the anchor pad having an opposing first selective attachment surface facing away from the adhesive surface, the first selective attachment surface including a hook portion of a hook and loop fastener. The method also includes attaching a first portion of a tension member having a second selective attachment surface to the first selective attachment surface of the anchor pad, the second selective attachment surface includes the loop portion of the hook and loop fastener. The method also includes displacing adipose tissue from a natural position to a displaced position and maintaining the adipose tissue in the displaced position with the tension member.

In another exemplary aspect, the present disclosure is directed to a method of maintaining a pannus on a patient in a displaced position during a medical procedure to provide access to a body region of the patient with a tissue retention system. The method includes adhesively adhering directly to a patient's abdomen an adhesive surface of a first anchor pad, the first anchor pad having a pad length and a pad width, the first anchor pad having an opposing first selective attachment surface facing away from the adhesive surface. The method also includes adhesively adhering a second anchor pad at an anchoring location spaced from the first anchor pad and includes attaching a first portion of a tension member having a second selective attachment surface to the first selective attachment surface of the anchor pad without adhesively adhering the tension member directly to the patient's skin. Adipose tissue on the abdomen is displaced from a natural position to a displaced position. A second portion of the tension member is attached to the second anchor pad so that the tension member is in tension between the first and the second anchor pads. The adipose tissue is maintained in the displaced position with the tension member.

In another exemplary aspect, the present disclosure is directed to a method of maintaining adipose tissue on a thigh of a patient in a displaced position during a medical procedure.

In another exemplary aspect, the present disclosure is directed to a method of maintaining a breast on a patient in a displaced position during a medical procedure to provide access to a body region of the patient with a tissue retention system.

In another exemplary aspect, the present disclosure is directed to a method of maintaining buttocks on a patient in a displaced position during a medical procedure to provide access to a body region of the patient with a tissue retention system.

In another exemplary aspect, the present disclosure is directed to a method of maintaining adipose tissue on a patient in a displaced position with a tissue retention system during a child birthing procedure to provide access to the abdominal region of the patient. The method includes scrubbing the abdomen with a cleanser and removing a backing from a flexible anchor pad to expose an adhesive surface of the anchor pad, the anchor pad having an opposing first attachment surface facing away from the adhesive surface. The method includes adhesively adhering directly to the patient's lower abdomen the adhesive surface of the anchor pad. It should be noted that the in some instances, the pannus can be scrubbed or prepped directly through the porous anchor pads after the anchor pads are in place. A first portion of a tension member having a second selective attachment surface is attached to the first selective attachment surface of the anchor pad. Adipose tissue is displaced from a natural position to a displaced position using the support member to pull the anchor pad and abdomen. The adipose tissue is maintained in the displaced position with the tension member.

In another exemplary aspect, the present disclosure is directed to a method of maintaining adipose tissue on a patient in a displaced position with a tissue retention system during a femoral catheterization procedure to provide access to the femoral region of the patient. The method includes adhesively adhering directly to a patient's skin adjacent the adipose tissue an adhesive surface of an anchor pad, the anchor pad having an opposing first attachment surface facing away from the adhesive surface. A first end of a tension member having a second selective attachment surface is attached to the first selective attachment surface of the anchor pad. Adipose tissue is displaced from a natural position to a displaced position, and the adipose tissue is maintained in the displaced position with the tension member. A portion of the femoral region of the patient is cleansed and a needle is introduced through the cleansed portion of the femoral region of the patient.

In another exemplary aspect, the present disclosure is directed to a method of applying pressure to a femoral artery on a patient after a femoral catheterization procedure. The method includes the steps of adhesively adhering directly to a patient's skin adjacent tissue on a patient's thigh an adhesive surface of an anchor pad. The anchor pad has an opposing first selective attachment surface facing away from the adhesive surface. The method also includes attaching a first end of a tension member having a second selective attachment surface to the first selective attachment surface of the anchor pad. A force is applied through the tension member to cause pressure to be applied to the incision in the femoral region of the patient. In a further aspect a sterile pad may be placed over the incision to control bleeding and/or intensify the pressure on the incision. Further, a second anchor pad may be applied and the tension member will be attached to the second pad to maintain the applied tension.

In another exemplary aspect, the present disclosure is directed to a kit for performing a catheterization procedure on a patient having an excess of adipose tissue in an abdominal region of the patient. The kit includes a needle sized to puncture the patient's skin, a flexible hollow tube for threading through the femoral artery, and a flexible anchor pad having a length and width. The anchor pad includes a pad body with an adhesive surface thereon, the adhesive being configured to selectively adhere to a patient's skin adjacent the adipose tissue. It also includes an opposing first attachment surface facing away from the adhesive surface, the first attachment surface including one of a hook and loop portion of a hook and loop fastener. The kit includes a flexible tension member having a second attachment surface, the second attachment surface including the other of the hook and loop portion of a hook and loop fastener, the tension member having a width less than the width and less than the length of the anchor pad such that loading onto the anchor pad from the support member is distributed over an area of the skin greater than the area of the overlap of the first and second attachment surfaces.

In another exemplary aspect, the present disclosure is directed to a kit for a medical professional performing a medical procedure. It includes a cotton tip applicator, pads, gauze, suction tubing, and a Foley catheter. It also includes a plurality of anchor pads each having a pad length and a pad width. Each anchor pad includes a pad body with an adhesive surface thereon, the adhesive being configured to selectively adhere to a patient's skin, and includes an opposing first attachment surface facing away from the adhesive surface, the first attachment surface including hook portion of a hook and loop fastener. The kit also includes a tension member having a second attachment surface, the second attachment surface including a loop portion of a hook and loop fastener. The tension member has a tension member width less than the pad width and less than the pad length of the anchor pad such that loading onto the anchor pad from the support member is distributed over an area of the skin greater than the area of the overlap of the first and second attachment surfaces.

In another exemplary aspect, the present disclosure is directed to a tissue retention system to assist in maintaining adipose tissue on a patient in a displaced position during a medical procedure. The tissue retention system includes a flexible anchor pad having a pad length and a pad width. The anchor pad includes a pad body with an adhesive thereon, the adhesive being configured to selectively adhere to a patient's skin and includes an opposing first attachment surface facing away from the adhesive surface. The system also includes a flexible tension member having a second attachment surface configured to selectively attach to the first attachment surface.

In another exemplary aspect, the present disclosure is directed to a method of maintaining adipose tissue on a patient in a displaced position during a medical procedure to provide access to a body portion of the patient with a tissue retention system. The method may include adhesively adhering directly to a patient's skin at a displacement site an adhesive surface of an anchor pad, the anchor pad having an opposing first selective attachment surface facing away from the adhesive surface. A first portion of a tension member having a second selective attachment surface is attached to the first selective attachment surface of the anchor pad without adhesively adhering the tension member directly to the patient's skin. Adipose tissue is displaced from a natural position to a displaced position, and the adipose tissue is maintained in the displaced position with the tension member.

In a further aspect, the displacement site on the skin includes a first anchor pad and the retention system includes at least two additional anchor pads. In this embodiment, a first tension member is releasably attached to the first anchor pad and is releasably connected to a second anchor pad spaced from the displacement site. A second tension member is releasably connected to the first anchor pad and is releasably connected to a third anchor pad spaced from the displacement site and the second anchor pad. The first tension member extends in a first direction and the second tension member extends in a second direction such that the displacement site can be displaced at in least in part in both the first and second directions.

Further aspects, forms, embodiments, objects, features, benefits, and advantages of the present invention shall become apparent from the detailed drawings and descriptions provided herein.

BRIEF DESCRIPTION OF THE DRAWINGS

FIGS. 1a and 1b are illustrations of an exemplary tissue retention system according to one embodiment of the present invention.

FIG. 4 is an illustration showing an alternative method of maintaining the pannus in a displaced position with the tissue retention system by attaching the tissue retention system to an operating table.

DETAILED DESCRIPTION

Figure 1B:
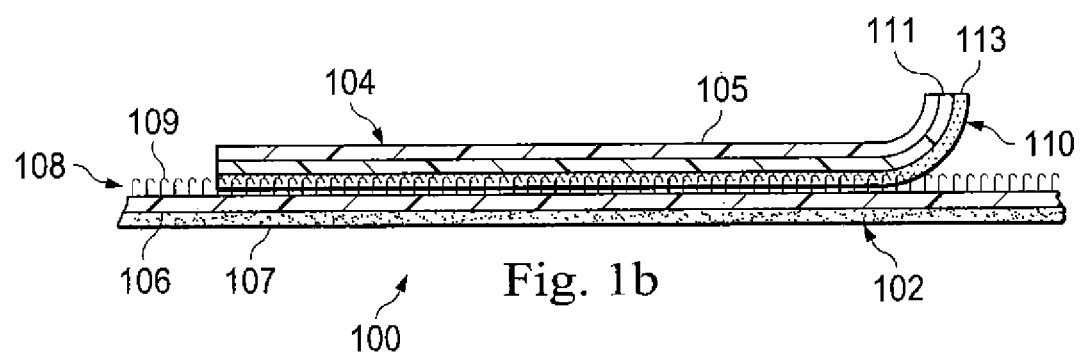

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Adipose tissue may hinder treatment during other routine or non-routine treatment. For example, in some instances, adipose tissue may detrimentally affect visualization or other access to perform procedures, such as, for example, panniculectomys, to treat panniculitis, general wound care, femoral catheterization, tracheal intubation, cesarean sections, hysterectomies, among other medical procedures.

The tissue retention system disclosed herein maintains adipose tissue in a position that provides better access to patient body regions requiring treatment. For example, it may be used to displace or secure adipose tissue, such as the abdominal apron or pannus, out of the lower abdomen or groin region during child birthing to provide better visualization and easier access to an attending health care provider.

Skin is composed of multiple layers. The main layers comprise the epidermis layer, the dermis layer, and subcutaneous tissue. The epidermis layer comprises sublayers including stratum corneum, stratum ludidum (not present in thin skin, only thick, hairless skin of palms & soles), stratum granulosum, stratum spinosum, and stratum germinativum. The tissue retention system disclosed herein is a non-penetrating solution that adheres to the epidermal layers of the skin without adhering to the dermis or subcutaneous tissue to displace adipose tissue while maintaining skin integrity. Further, certain aspects do so without penetrating or pinching tissue to obtain skin anchorage, unlike hooks or other skin gripping systems, which can damage the skin. Instead, it is flexible enough to conform to natural curves of the anatomy, without major tissue deformation or penetration.

While the emphasis of this discussion is on retention of the pannus for child birthing, it is noted that the present tissue retention system has application in displacing or maintaining adipose tissue of other body regions for many different medical applications, only some of which are discussed herein. As alternative use and variation is shown in U.S. patent application Ser. No. 11/743,858, filed May 3, 2007, titled "Apparatus and Method of Inhibiting Perianal Tissue Damage" is incorporated herein in its entirety.

Turning now to FIGS. 1a and 1b, the tissue retention system, referenced herein by the numeral 100, includes an anchor pad 102 and a tension member 104. As discussed in greater detail below, the anchor pad 102 is configured to attach directly to a patient's skin, such as adjacent adipose tissue, and the tension member 104 releasably attaches to the anchor pad to maintain the anchor pad 102 and the attached skin in a position that provides visualization or access to a body region for a medical procedure.

The anchor pad 102 includes a pad body 106 and an attachment surface 108. A biocompatible adhesive layer 107 is disposed on the pad boy 106 and is configured to adhere directly to a patient's skin or an inanimate surface. In some embodiments, the adhesive of the adhesive layer 107 is configured to easily release from the patient's skin with minimal damage or soreness after a medical procedure is complete. In some embodiments, prior to use, the adhesive layer 107 faces a non-stick backing (not shown) that can be peeled away to reveal the adhesive layer 107 on the pad body 106. In one embodiment, the anchor pad 102 is formed of a material known as Gamma Stable Hook Fastener with Adhesive with a product number of 7333 sold by 3M of St. Paul, Minn. Examples of suitable adhesives include, without limitation, acrylic adhesives, silicone based adhesives, urethane adhesives, synthetic or natural rubber adhesives, among others.

The attachment surface 108 is configured to face away from the patient's skin and provides an interfacing surface to releasably fasten to the tension member 104. The attachment surface 108 includes a releasable fastening feature, that may be, for example, a part of a hook and loop fastening system or a releasably adhesive system. While hook and loop fastening systems are disclosed as being used in the illustrated embodiments, it is contemplated that in further embodiments alternative releasable fastening mechanisms are employed. For example, such releasable fastening systems have a greater shear strength than peel strength and may include, but without limitation to alternative structures, magnetic couplings, specialized adhesives, ratchet teeth, and directional specific fibers. In the exemplary embodiment shown, the fastening feature comprises hooks 109 of a relatively rigid hook portion of the hook and loop fastening system. As shown in FIG. 1a, the fastening feature is included over substantially the entire attachment surface 108 of the anchor pad 102 as a plurality of hooks 109.

In one embodiment, the anchor pad 102 is at least partially flexible and conforms to contours of a patient's body shape. For example, the pad 102 is sufficiently flexible to conform about a patient's curved abdominal apron or along a patient's curved thigh. It may have the rectangular shape shown, or may have other alternative shapes, such as circular, crescent, oval, triangular, or any other suitable shape. In the exemplary embodiment shown, the anchor pad 102 includes rounded corners that enable the anchor pad 102 to more comfortably adhere to the patient's skin and are less likely to cause irritation. In the exemplary embodiment shown, the anchor pad 102 includes a width $W_p$ and a length $L_p$ with the width $W_p$ being greater than the length $L_p$. In some embodiments, the width $W_p$ is in the range of 5-14 inches long and the length $L_p$ is in the range of 4-8 inches long. In other embodiments, the width $W_p$ is in the range of 7-8 inches long and the length $L_p$ is in the range of 5-6 inches long. Thus, in some aspects, the anchor pad 102 has an area ranging from 20 to 112 square inches. Other dimensions, both larger and smaller, are also contemplated.

The adhesive used to form the adhesive layer 107 is selected to have material properties permitting it to be peeled from the patient's skin after the procedure is complete by pulling a corner or edge from the skin at an angle from the skin within a range from about 10 to 170 degrees without damaging the skin. In addition, the anchor pad 102 and adhesive can be removed without damaging the skin without the use of water, soap, solvent or other releasing material. In some embodiments, the adhesive is selected to have an adhesion to LDPE, 180 Degree peel of 15-50 oz/inch width, and more particularly, about 20-50 oz/inch width, and more particularly, about 30-40 oz/inch width, and even more particularly, about 35-37 oz/inch width. The adhesive may be a skin-friendly, rubber based adhesive. Further, both the anchor pad 102 and the tension member 104 are latex free. Further, the adhesive is configured so that in some embodiments, less than 10% of the adhesive forming the adhesive layer remains on the skin as residue. In other embodiments, less than 5% of the adhesive forming the adhesive layer remains on the skin as residue.

The tension member 104 includes a flexible outer material 105, a body portion 111, and an attachment surface 110 with a fastening feature formed thereon. Here the fastening feature is a plurality of generally soft fiber loops 113. In one embodiment, the fastening feature is included over substantially the entire attachment surface 110 of the tension member 104. In one aspect, the body portion 111 with the fiber loop attachment surface 110 is a material known as Gamma Stable Loop with Adhesive with a product number of 7331 sold by 3M of St. Paul, Minn. In one aspect, the flexible outer material 105 is a material known as optiFLEX SELECT® manufactured by FLEXcon. In some embodiments, the outer material 105 is formed of a polyethylene material, and the body portion 111 is formed of a nylon material.

In some embodiments, the tension member is non-distensible. Accordingly, in these embodiments, the tension member is substantially non-distensible in its longitudinal direction and flexible in at least one axis deviating from the longitudinal axis. In other embodiments however, the tension member is distensible. Accordingly, in these embodiments, the tension member is at least partially distensible in its longitudinal direction and also flexible in at least one axis deviating from the longitudinal axis. In some embodiments, the materials forming the tension member are selected so that the tension member yields more than 20% of its length under tension loads up to 60 force pounds. In some embodiments, it yields more than 10% of its length under tension loads up to 60 force pounds. In other embodiments, it yields more than 2% of its length under tension loads up to 60 force pounds. In some embodiments however, the tension member does not yield, but elastically deforms to increase length under load and return to its original length when the load is removed. It should be noted that the tension member may include substantially homogonous or substantially uniform material properties along its length.

Material properties and structure of the tension member 104 determine its yield strength or elasticity. For example, the width, thickness, and material of the outer material 105, (in combination with the other layers of the tension member 104) may be selected to provide desired yield and elasticity characteristics. Furthermore, these may be selected to cooperate with the adhesive and size of the anchor pad 102 so that, in use, the tension member 104 stretches before the anchor pad 102 begins to detach from the patient's skin. In the following descriptions, the hook and loop fastener is designed to hold the described shear load without failure. For example only, in embodiments where the anchor pad 102 has adhesive properties such that it begins to detach from the patient's skin at peel loads of three oz/inch width at 180 degree peel, then the tension member 104 may be designed to elongate either elastically or in-elastically at loads less than three oz/inch width applied at 180 degrees. Accordingly, in embodiments having a pad width of 5 inches, loads of 15 oz at 180 degrees are required to peel the anchor pad at 180 degrees. This example however, is not limiting as it is contemplated that other levels of adhesion also may be implemented. In some embodiments, an additional safety factor may be included, such that the outer material 105 (or the entire tension member 104) begins to stretch at, for example, loads less than 90% of the peel load. In other words, using the example above, the safety factor may be applied so that the outer material 105 begins to stretch at loads less than 90% of 15 oz at 180 degree peel or equivalently 13.5 oz. The safety factor may be 80%, 60%, or other factor between 0% and 100%.

In other embodiments, the tension member 104 elongates either elastically or in-elastically before the anchor pad 102 begins to damage the patient's skin, thereby avoiding blistering, delamination, or other damage that may occur by inadvertent overloading. As an example, if skin damage occurs under shear loads of 40 oz/in$^2$ of skin and the anchor pad 102 has an area of 12 in$^2$, then the tension member 104 may be formed so that the outer material 105 (or the entire tension member 104) stretches at loads less than 480 oz or equivalently at loads less than 30 lb. In some embodiments, an additional safety factor may be included, such that the outer material 105 (or the entire tension member 104) begins to stretch at, for example, loads less than 90% of the anchor pad area multiplied by the skin shear force. In other words, using the example above, the safety factor may be applied so that the outer material 105 begins to stretch at loads less than 90% of 12 in$^2$ multiplied by 40 lbs/in$^2$, equaling 432 oz or equivalently 27 lb. The safety factor may be 80%, 60%, or other factor between 0% and 100%. It is noted that the use of skin damage occurring at 40 oz/in$^2$ is merely an exemplary value, and skin damage may begin occur at loads much higher or much lower. The load value at which skin damage occurs may vary depending on the age of the patient, the location of the anchor pad on the body, the angle of the force applied, the amount of time the force is applied, the dwell time of the adhesive, skin properties such as porosity and moistness, and other factors. It is contemplated that the tension member may have properties that permit it to elastically or in-elastically elongate at loads of about 60 lbs in some embodiments. Elongation is considered to have occurred when the tension member stretches more than 2% of the length between anchoring points. In some embodiments, the tension member elongates at loads of about 40 lbs, while in other embodiments, at loads of about 30 lbs. In yet other embodiments, it elongates at loads of about 20 lbs. Further embodiments have properties that permit elongation at about 10 lbs. Other force amounts, smaller and greater than those identified also may be used. It should be noted that the tension member may include substantially homogonous or substantially uniform material properties along its length between the anchoring points. In other embodiments, minor interruptions in uniform properties also are contemplated.

In some embodiments, the outer material 105 is adhesively bonded to the body material 111 through a rolling process to form an integrated tension member 104, as shown in FIGS. 1a and 1b. In these embodiments, the yield strength or elasticity of the outer material 105 and the body material 111 together, or likewise, the entire tension member 104 may be arranged so that, in use, the tension member 104 elastically or in-elastically stretches before the anchor pad begins to slip or damage the patient's skin, as discussed above.

In some embodiments, the tension member is designed to carry tension loads, but to not carry compression loads. Accordingly, it can be folded or rolled for packaging, and then unfolded or unrolled for use, having properties as a non-distensible or distensible fabric material of the described structure.

The tension member 104 has a width $W_s$ and a length $L_s$ with the width $W_s$ being less than the length $L_s$. In some embodiments, the width $W_s$ of the tension member 104 is sized within a range of 1 and 5 inches. In other embodiments, the width $W_s$ is within a range of 2-4 inches, and in yet other embodiments, the width $W_s$ is about 3 inches. The length $L_s$ is considerably longer than the width $W_s$ to enable the tension member to extend from the anchor pad 102 as shown in FIG. 1b to a second anchoring location either on the patient or on some other structure, as discussed below. In some embodiments, the width to length ratio of the tension member 104 is between the range of 1:5 to 1:50. Other ratios outside this range also are contemplated.

The tension member length $L_s$ is greater than its width $W_s$ and is used with the anchor pad 102 to maintain displaced adipose tissue in a less-obtrusive position during a medical procedure. The fastening feature on the attachment surface 110 interfaces with the fastening feature on the attachment surface 108 of the anchor pad 102. As described above, in the exemplary embodiment shown, the fastening feature of the tension member 104 is the loop of a hook and loop fastening system. Accordingly, the loop portion of the tension member 104 selectively attaches to the hook portion on the anchor pad 102. In some embodiments, the fastening feature covers the entire surface of the tension member 104. This enables simple attachment without consideration for whether the tension member is too large or small for any given patient.

In the embodiment shown, the hooks 109 on the attachment surface 108 of the anchor pad 102 face away from a patient's skin and the loops 113 on the attachment surface 110 of the tension member 104 that face toward a patient's skin. Thus, only the softer loop portion of the fastening system directly contacts the patient's skin. This may avoid some discomfort that may occur if the hook portion of the fastening system were placed against the patient's skin. In other embodiments however, the loops are disposed on the anchor pad and the hooks are disposed on the tension member.

Referring to FIG. 1a, the width $W_s$ of the tension member 104 is shown as less than the width $W_p$ of the anchor pad 102. In some embodiments, the ratio of the width $W_p$ of the anchor pad 102 to the width $W_s$ of the tension member 104 is within a range of 1.5:1 to 4:1. In some embodiments, the ratio of the width $W_p$ of the anchor pad 102 to the width $W_s$ of the tension member 104 is within a range of 2:1 to 3.5:1. Other ratios, both larger and smaller than those identified here also are contemplated.

The anchor pad 102 and tension member 104 together define an overlap area represented by the area of the tension member 104 that is selectively fastened to the anchor pad 102. FIG. 1a shows this overlap area having a length Lo which is the maximum length of the tension member 104 fastened to the anchor pad 102 and having an overlap width Wo which is the maximum width of the tension member 104 fastened to the anchor pad 102. In FIG. 1a, the overlap length Lo and the overlap width Wo are substantially the same as the respective anchor pad length $L_p$ and the tension member width Ws. However, the overlap area may differ from that shown and is dependent upon where the tension member 104 is placed on the anchor pad 102. Furthermore, it is contemplated that in alternative embodiments, the width of the fiber loops 113 is less than the width of the tension member 104. Thus, in these embodiments, the overlap area (defined as the area of the tension member that is selectively fastened to the anchor pad) is less than the area of the tension member that overlies, but does not fasten to, the anchor pad 104. In some embodiments, the ratio of anchor pad area to overlap area is within a range of 1:1 to 6:1. In other embodiments, the ratio is within a range of 1.5:1 to 5:1, and in yet other embodiments, the ratio is within a range of 2:1 and 4:1.

In some embodiments, the tension member 104 and the anchor pad 102 are selected so that when fastened together, they have a 135 degree closure peel strength average within a range of about 1-10 oz/inch width and more particularly, within a range of about 1-8 oz/inch width, and more particularly about 2-6 oz/inch width. In other embodiments, they are selected to have a 135 degree closure peel strength average within a range of about 3 oz/inch width. It is contemplated that in high tension applications of one embodiment, the 135 degree closure peel strength is approximately 32 oz/inch width. In a preferred embodiment, the adhesive to skin peel strength is greater than the closure peel strength. For example, in one aspect, the skin peel strength is at least twice as great as the closure peel strength. In a further embodiment, the hook and loop closure peel strength is less than 50%, and preferably less than 25%, of the adhesive to LDPE, 180 Degree peel of the anchor pad adhesive. Still further, the shear strength of the hook and loop fastening system described herein is substantially greater than the closure peel strength. For example, the shear force applied to the tension member/anchor pad overlap area described above can be as high as 80 pounds while the hook and loop closure peal strength at 135 degrees is less than 10 oz/inch width. Thus, in one aspect, the force needed to decouple the hook and loop fastening assembly is less than 20 oz. while the shear strength to hold tissue is at least as large as 80 pounds.

The tension member 104 has a length $L_s$ long enough to extend from a patient's abdominal region, around the patient's shoulder or neck and back to the abdominal region. In some embodiments, the tension member 104 has a length long enough to extend from the patient's abdominal region to an area above the patient's head to attach to a stable structure, such as a surgical bed. The anchor pad 102 and the tension member 102 may be formed of a non-radiopaque material permitting it to be used without affecting radiology processes or treatments. Still further, in one aspect, the tension member 104 is generally inelastic in its central longitudinal axis and flexible in at least one axis deviating from the central longitudinal axis.

In use, the anchor pad 102 attaches to the patient's skin in an area adjacent to loose or adipose body tissue. The tension member 104 attaches to and extends from the anchor pad 102 in a direction that the adipose tissue is to be displaced. It may be anchored on a second anchor pad securely disposed for such a purpose. For example, the second anchor pad may be disposed on the patient's body, such as along the patient's shoulder, or may be anchored to a structure, such as a stable portion of a surgical table. In some embodiments, the tension member 104 extends about the shoulder or neck of the patient and back to the first anchor pad 102 or one adjacent to it. By attaching the tension member at both ends in tension, displaced excess tissue may be maintained in a desired position. Furthermore, the tension member 102 may be attached and secured in place before an incision is even made.

Because in the embodiment shown, the anchor pad 102 has a width greater than the width of the tension member 104 or attachment area of the tension member, the anchor pad 102 acts to laterally distribute loading from the tension member 104 along an area of adipose tissue having a greater width than the overlap area. Further, because the attachment surface 108 of the anchor pad 102 includes the attachment features, which in the example shown are hooks 109 of a hook and loop fastener, the tension member 104 is disengaged from the anchor pad 102 and reattached with little effort in a different location on the anchor pad 102, permitting easy tension member adjustment to an infinite number of locations on the anchor pad 102. Naturally, this same adjustment to any of an number of locations may be made on the tension member 104 and the second anchor pad disposed spaced apart from the anchor pad 102. Still further, once the tension member 104 is engaged to pad 102, the attached adipose tissue will be held in a desired location. Some examples of the tissue retention system in use will be described with reference to FIGS. 2-9.

Figure 2:
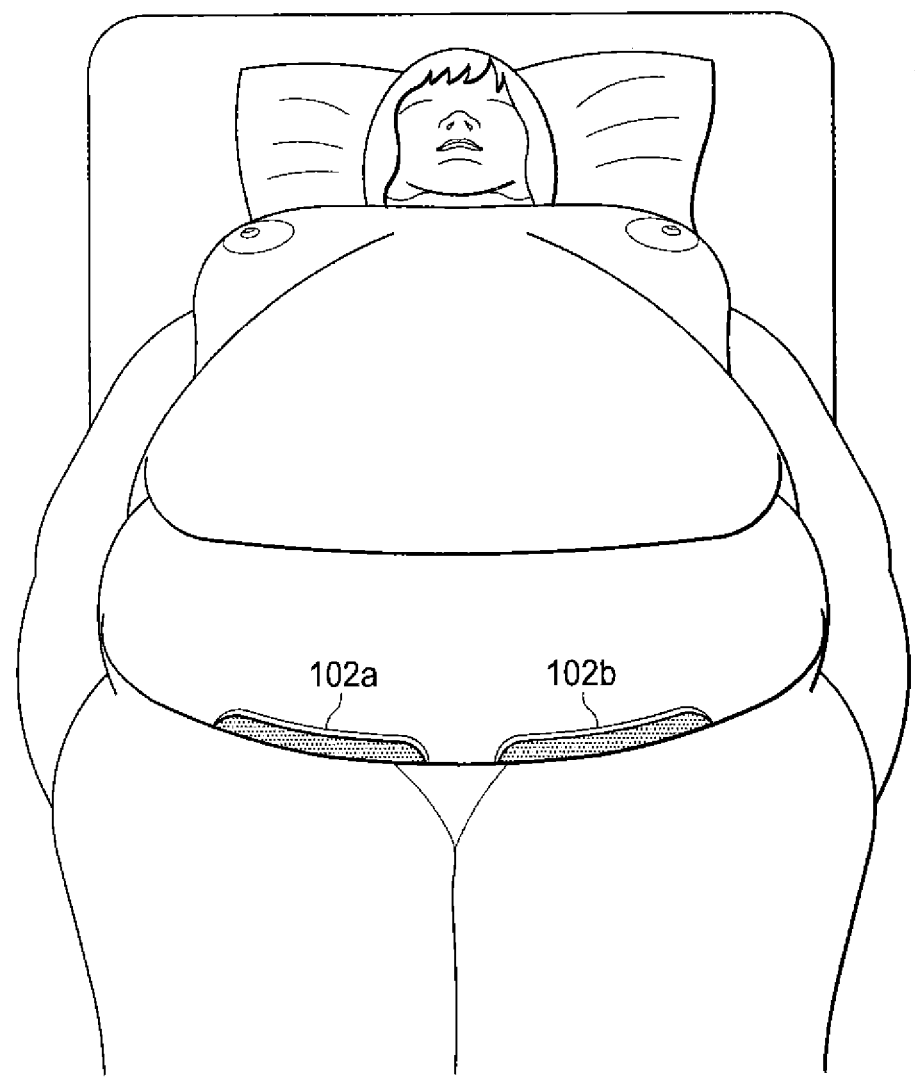
FIG. 2 is an illustration of an obese patient showing the pannus or abdominal apron with attached anchor pads of the exemplary tissue retention system.

FIG. 2 shows an example of an obese patient lying on a hospital surgical table in a position for a surgical procedure, such as, for example, a cesarean section. The procedure includes placing the patient on the operating room table per protocol, generally in supine position with a left lateral tilt. The arms may be secured using a loose tension member on arm boards. As shown, the patient has a pannus or abdominal apron entirely covering the lower abdomen. In order to perform the procedure, the operating physician is required to expose the lower abdomen by displacing the pannus. The physician or other medical personnel may lift the pannus and then scrub the abdomen per hospital policy with a cleanser such as alcohol or Betadine scrub. It is contemplated, however, that in some instances, a part of or the entire pannus displacement procedure, as described below, may occur prior to scrubbing or prepping the pannus. The adhesive described above maintains its adhesion in the presence of cleansers such as alcohol and Betadine scrub.

A backing material may be removed from an anchor pad 102 to expose the adhesive layer 107 (FIG. 1b) of the anchor pad 102. The anchor pad 102 is then be applied directly to the skin on the lower abdomen so that the adhesive 107 on the anchor pad 102 securely adheres it to the skin. Care should be taken to not place the anchor pad 102 over skin intended for incision. In the example in FIG. 2, two anchor pads 102a, 102b have been applied to the underside of the pannus so that an upper portion, such as for example about a third of each anchor pad, protrudes outwardly from the folds of skin. Also, in the example in FIG. 2, the anchor pads 102a, 102b are applied so that the width lies relatively perpendicular to the direction that the adipose tissue is to be displaced. Additional anchor pads (not shown) may be placed at additional locations on or about the patient. In some embodiments, the additional anchor pads may be disposed on the patient's shoulders. These additional anchor pads also serve to connect to the tension member 104 as described below.

Figure 3A:
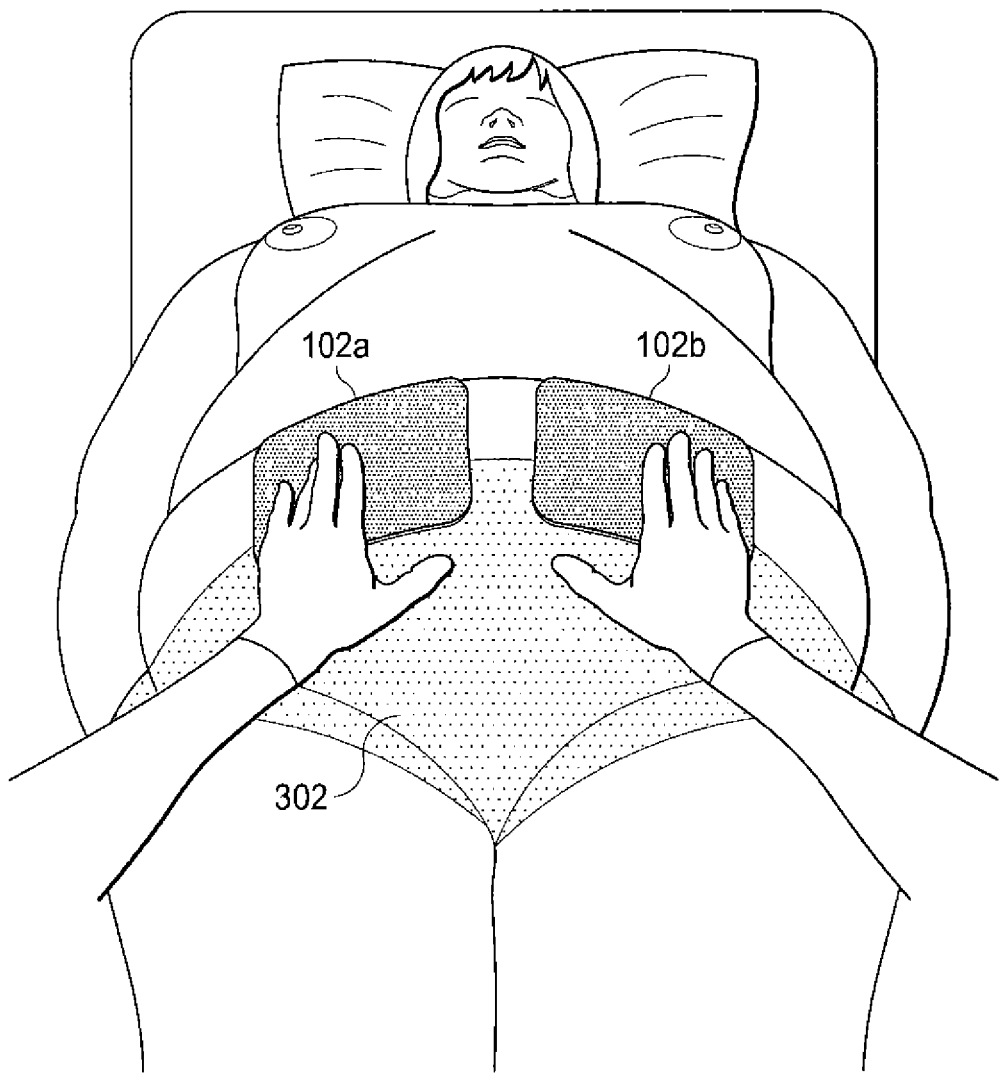
FIGS. 3a-3c are illustrations of an application of the exemplary tissue retention system to maintain the pannus in a displaced position.

Turning now to FIG. 3a, in some embodiments, medical personnel manually lift the pannus away to expose the lower abdomen where the cesarean section will be performed. In such situations, the medical personnel place fingertips on the anchor pad 102 rather than on the bare skin to distribute point loads applied by fingers against the pannus, thereby reducing the chance of bruising. The medical personnel hold the pannus in place until the tension member 104 (see FIG. 3b) is utilized.

Figure 3B:
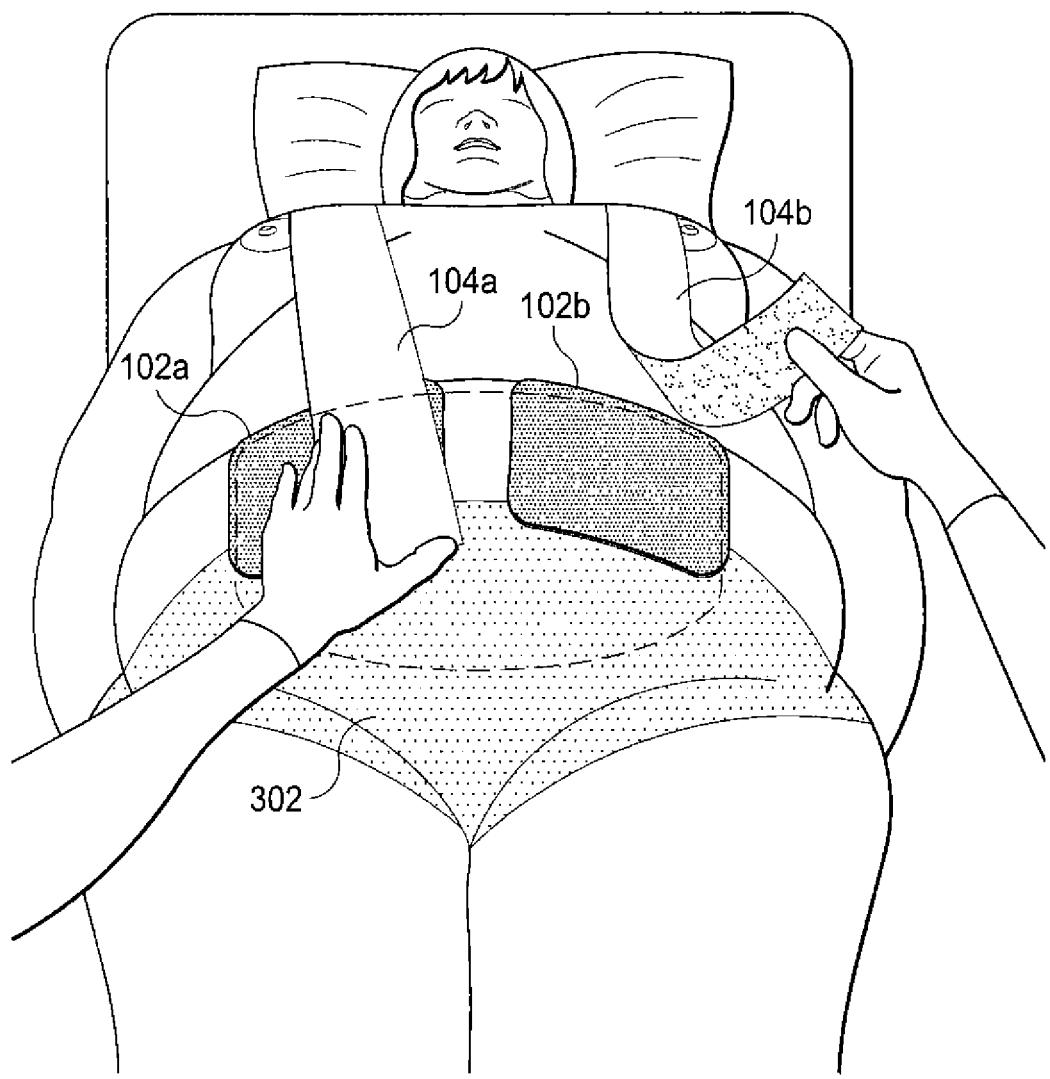

FIG. 3b shows tension members 104a, 104b replacing the medical personnel to maintain the pannus in a desired position. In the embodiment shown, one end of the tension member 104a is attached to the anchor pad 102a on the pannus while the other end of the tension member 104 is tensioned and attached to a second anchor pad (not shown) disposed on the patient's shoulders. Here, as discussed above, the anchor pad 102a includes a hook material and the tension member 104a includes a loop material. As is apparent from FIG. 3b, a second tension member 104b attaches in tension to the anchor pad 102b and extends to a second anchor pad (not shown) disposed on the patient's shoulder. The dashed line in FIG. 3b shows an exemplary location where the anchor pads 102 may be placed to secure the pannus. However, it is contemplated that the anchor pads may be placed in regions outside the dashed line, including the supra pubic region of the body. The shaded area 302 represents an area that is normally hidden where the skin of the pannus rests against the skin of the lower abdomen.

In some embodiments, the tension member 104 does not attach to anchor pads disposed on the patient's shoulders or other body portion, but may extend behind the patient's neck or about the patient's shoulder and return to one of the anchor pads 102a, 102b disposed on the pannus. Thus, a single tension member may be used to secure the pannus. For example, referring to FIG. 3b, in such an embodiment, the tension member 104a and 104b are ends of a single tension member extending behind the patient's neck.

Figure 3C:
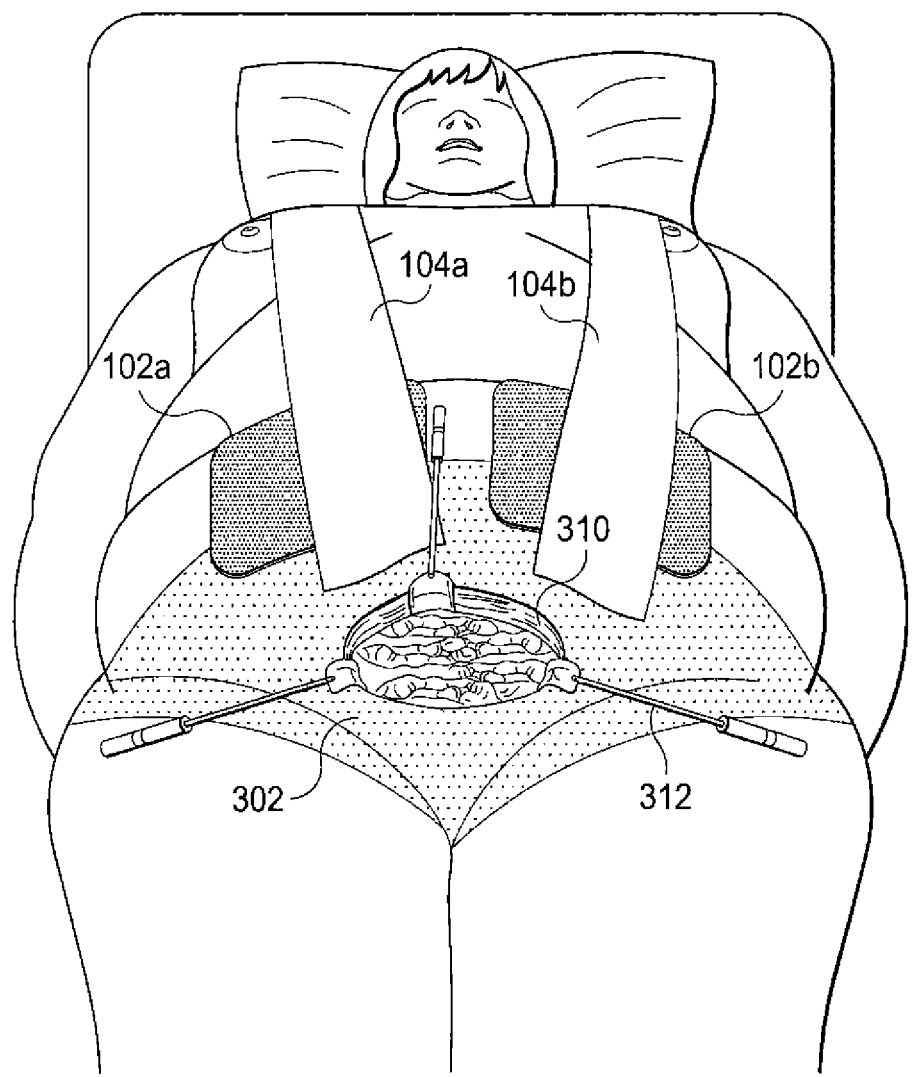

FIG. 3c shows the pannus displaced and maintained in position by the tension members 104a 104b, thereby exposing the lower abdomen for the surgical procedure. Because the tension members 104a, 104b were placed in tension, the tension members 104 securely hold the anchor pads 102 in place, and therefore, also holds the pannus in a specific position.

During or while still preparing to perform the medical procedure, the tension members 104a, 104b may be adjusted relative to the anchor pads 102a, 102b. This is accomplished by simply manually supporting the pannus while detaching one of the tension members 104a, 104b from the relative anchor pad 102a, 102b, moving the pannus and/or the tension member to the desired position, and reattaching the tension member to the anchor pad. In some embodiments, detaching the tension member from the anchor pad is simply accomplished by pulling the tension member to detach the attachment features, such as the hook and loop portions. The tension member is then re-attached at the desired location. Adjustment also may be made by detaching the tension member 104 from the anchor pad (not shown) disposed on or about the patient's shoulder. In this way, the tension member may be detached from the anchor pad, and the pannus can be adjusted simply by manipulating the tension member 104.

As shown for example in FIG. 3c, the anchor pad width is greater than the tension member width. Further, the anchor pads are disposed on the patient with a longer end extending laterally and the direction of the tension member extending longitudinally along the patient and substantially transverse to the longitudinal axis of the anchor pad. This provides a maximum level of load distribution to the skin at the displacement site in the regions lateral to the tension member, providing minimal discomfort to the patient.

Once the adipose tissue is securely displaced to expose the surgical site, medical personnel perform the medical procedure. For example, in one exemplary procedure, such as a cesarean section, the initial steps of pre-positioning the adipose tissue includes exposing the surgical site where the surgical procedure will be performed as explained above. The incision site is then prepared. An incision, such as a transverse incision, a midline incision, or other suitable incision, is made in the lower abdomen as shown by an opening 310 in FIG. 3c. In one aspect, after making the incision, one or more retractors 312 are positioned in the incision. A blade of the retractor is inserted through the skin into the incision to further enlarge the size of the opening 310 to that illustrated in FIG. 3c and/or to retract fat, muscle, blood vessels, and other structures below the surface of the skin. A surgical assistant can hold the handle of the retractor to maintain retraction. The procedure continues with the baby being born through the opening 310. Any retractors used during the procedure are removed from the incision. In some applications, such as child birthing, the change in the patient's abdominal size will naturally reduce the force on the tension members. However, if increased tension and/or a further reduction in tension is required, the force on tension members 104, 104b may be modified by momentarily disengaging the tension members from the anchor pads 102a, 102b. The tension members 104a, 104b are then reattached to the anchor pads 102a, 102b in an alternative tensioning position while further medical steps of the procedure are completed on the patient. For example, the placenta may be delivered through opening 310 while the tension members are in the alternative tensioning position. Eventually, the opening 310 is sutured closed. In a preferred method, once the surgical procedure is complete, the tension members 104a, 104b are de-tensioned and the anchor pads 102a, 102b are removed from the patient's skin.

Although described with reference to exposing the lower abdomen, it should be apparent that a similar method may be used to expose the groin region when access is required. This may be useful with some patients for hysterectomies and normal vaginal births of obese patients, for example. Still further, the retention system may be used for long term treatments to expose tissue 302 to speed healing and/or prevent infection.

Furthermore, although the method was described with medical personnel manually displacing the pannus with their hands prior to attaching the tension members 104a, 104b, it should be apparent that in some embodiments, the tension members 104a, 104b may be attached to the anchor pads 102a, 102b on the pannus prior to manually lifting the pannus to the desired position. In these instances, medical personnel take one end of the tension member 104 and place it on the anchor pad 102 by pressing firmly so they adhere together. Next, the medical personnel pull the tension member 104 to displace the abdominal pannus as far back as desired for the procedure, and then secure the other end of the tension member 104 to the second set of anchor pads.

FIG. 4 shows one example of the tension members 104a, 104b being used to connect to the pannus as described with reference to FIG. 3, but instead of attaching to the body at the second end, the tension members 104a, 104b are connected to adjacent structure. Here, additional anchor pads 102c, 102d are attached to a rigid or stable structure, such as a surgical table and provide an anchoring support for the pannus. Adhering the anchor pads to the table effectively eliminates two adhesive contact points on the patient. Other stable structures also may be used. As discussed above, the anchor pads 102a, 102b provide an unlimited number of anchor locations for the tension member 104. Likewise, the anchor pads 102c, 102d also provide such anchor location benefits. Accordingly, the tension member is adjustable at both ends where it is selectively coupled to an anchor pad joined to the patient or a fixed object. In an alternative embodiment not illustrated in the drawings, the tension member 104 includes an anchor pad that is fixedly coupled to one end. When it is intended for joining to the skin, the anchor pad fixedly joined to the tension member has a surface area and adhesive property similar to the anchor pads described above. If the anchor pad is intended for adhering to a fixed object, the area of the pad may be reduced and/or the adhesive strength may be increased. With the tension member having a fixed anchor pad on one end, the fixed anchor pad is fixed in a first location and the opposite end of the tension member is releasably coupled to a second anchor pad such as described above. Thus, in this embodiment, the system is only adjustable at one end. In still a further aspect, tension member 104b may be alternatively joined to anchor pad 102a. The tension member 104b may be pulled toward anchor pad 102d to further displace tissue near the displacement site at anchor pad 102a in a second direction. Thus, anchor pad 102a can be pulled toward anchor pad 102c and simultaneously pulled toward anchor pad 102d. This combination gives the user the ability to simultaneously mobilize adipose tissue near the displacement site in multiple directions to achieve the desired displacement.

Figure 5:
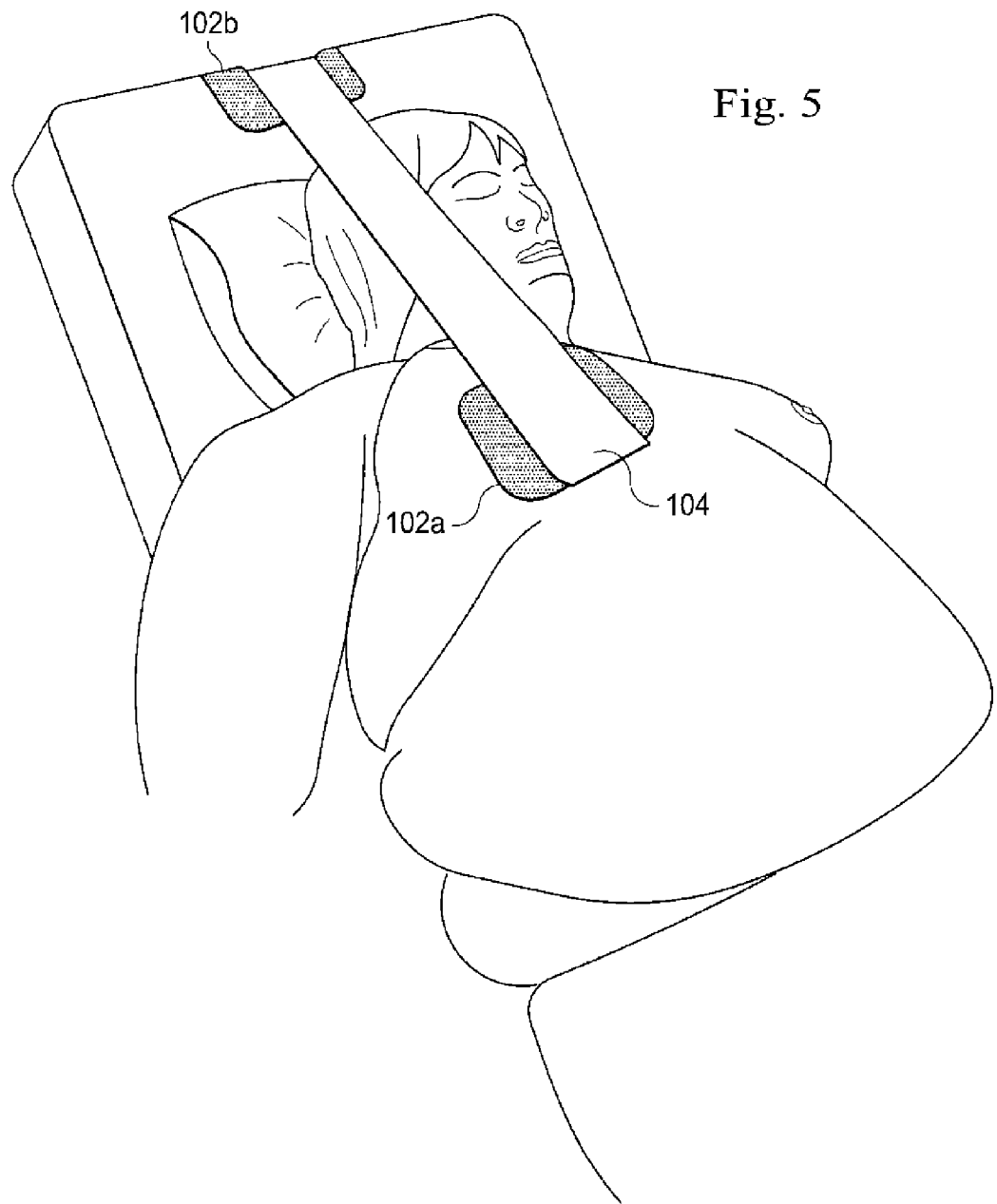
FIG. 5 is an illustration showing an exemplary application of the tissue retention system to maintain breast tissue of a patient in a displaced position.

FIG. 5 shows an alternative use of the tissue retention system 100. Here, a first anchor pad 102a is attached to the underside of a patient's large breast to support the adipose tissue and maintain it in a desired position. This is useful for example, in applications requiring surgical access or radiological tests. In some examples, the tissue retention system may be used for oncology purposes, including radiation treatment. This may enable positioning of the patient's flesh in substantially the same place each time the patient receives radiation treatment. In some instances, the breast may be displaced or otherwise secured to provide access to or around the breast during surgery. As shown in FIG. 5, the tension member 104 extends in tension between the first anchor pad 102a and a second anchor pad 102b—one attached to the patient's skin adjacent the adipose tissue and the other attached to a supporting structure, such as the bed.

Also, the retention system may serve as a breast compression system for obtaining mammographic images. An anchor pad can be adhered to the breast in the place of the plate 18 shown in U.S. Pat. No. 4,691,333 incorporated herein in its entirety. The anchor pad can include one or more radiopaque markers if desired to permit orientation. The tension member can then be applied to compress the breast for imaging and/or needle localization.

Figure 6:
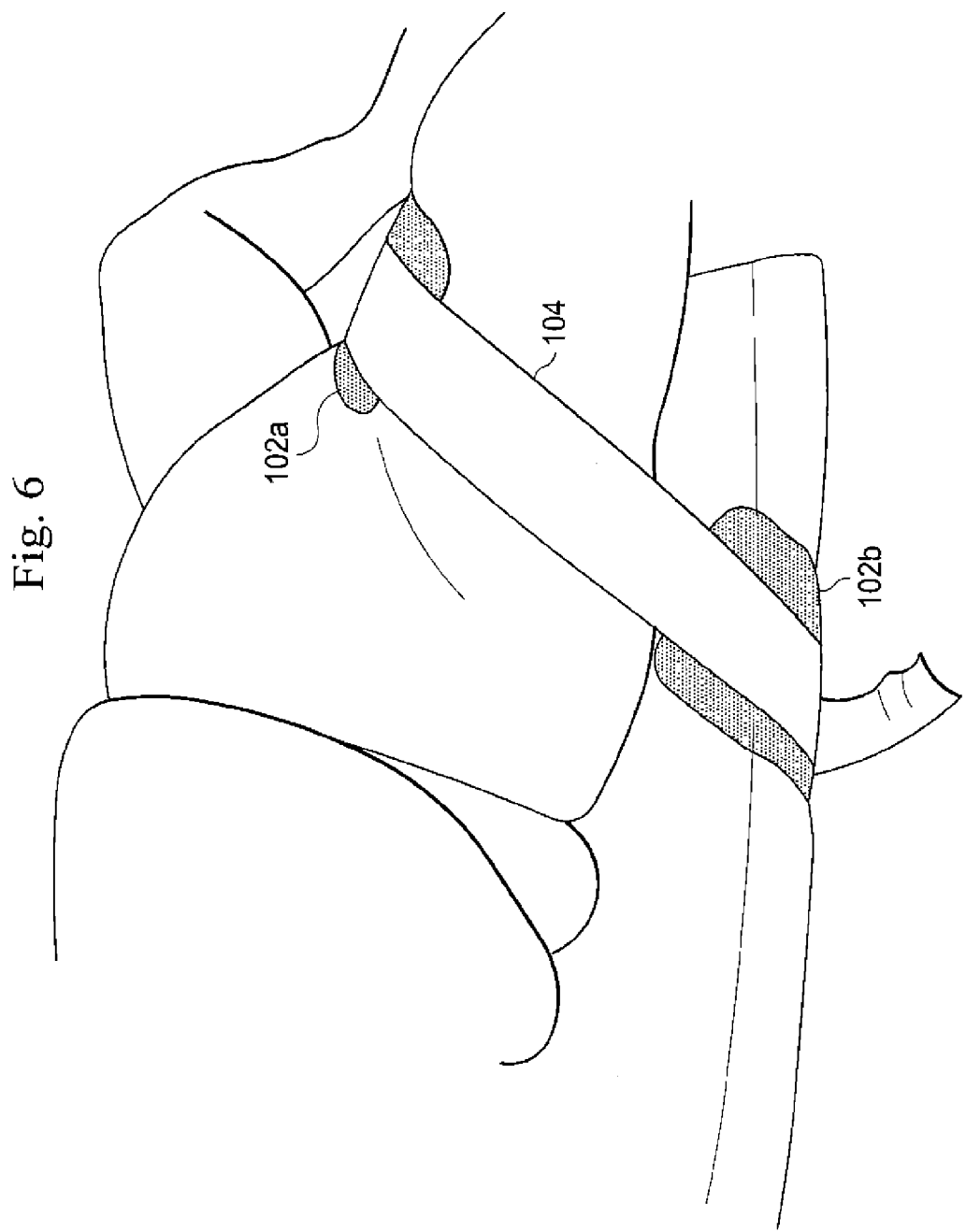
FIG. 6 is an illustration showing an exemplary application of the tissue retention system to maintain thigh tissue of a patient in a displaced position.

FIG. 6 shows other alternative uses of the tissue retention system 100. In one use, a first anchor pad 102a is attached to a patient's thigh in order to move the adipose tissue to provide access for a medical procedure. This may provide better visualization during repair or surgery of the groin, perineum, vaginal vault, or other areas needing better visualization under the adipose tissue. These applications may include general urology procedures. The tissue retention system 100 also can facilitate access to the femoral region for all types of cardiovascular procedures, ranging from angioplasty to using a Foley catheterization and to any type of thoracic surgery that requires catheterization of the femoral artery. In another use, the first anchor pad 102a is attached to a patient's thigh adjacent the femoral artery incision. A tension member is fix to the anchor pad 102a as a pressure bandage to apply pressure to the femoral artery incision after a femoral catheterization procedure. A sterile pad (not shown) may be placed directly over the femoral incision and the tension member can be applied to the sterile pad to compressively hold it in place. The sterile pad can control bleeding and acts to intensify the compression to the incision applied by the tension member. In this example, as in the example of FIG. 5 above, the tension member 104 extends in tension between first and second anchor pads 102a, 102b—one attached to the patient's skin adjacent the adipose tissue and the other attached to a supporting structure, such as the bed.

In the applications shown in FIGS. 5 and 6, the method may be similar to that described with reference to FIGS. 2-4 in that a backing is peeled from a first anchor pad 102a and the anchor pad is applied directly against the skin adjacent the adipose tissue to be displaced. The second anchor pad is disposed on the patient at an anchoring location or alternatively, on a support structure, such as the table or bed. The adipose tissue is displaced by hand and secured in place using the support member or is displaced by the support member 104 and secured in place. At any point, the support member may be simply adjusted to attach to another location on the anchor pad.

Figure 7:
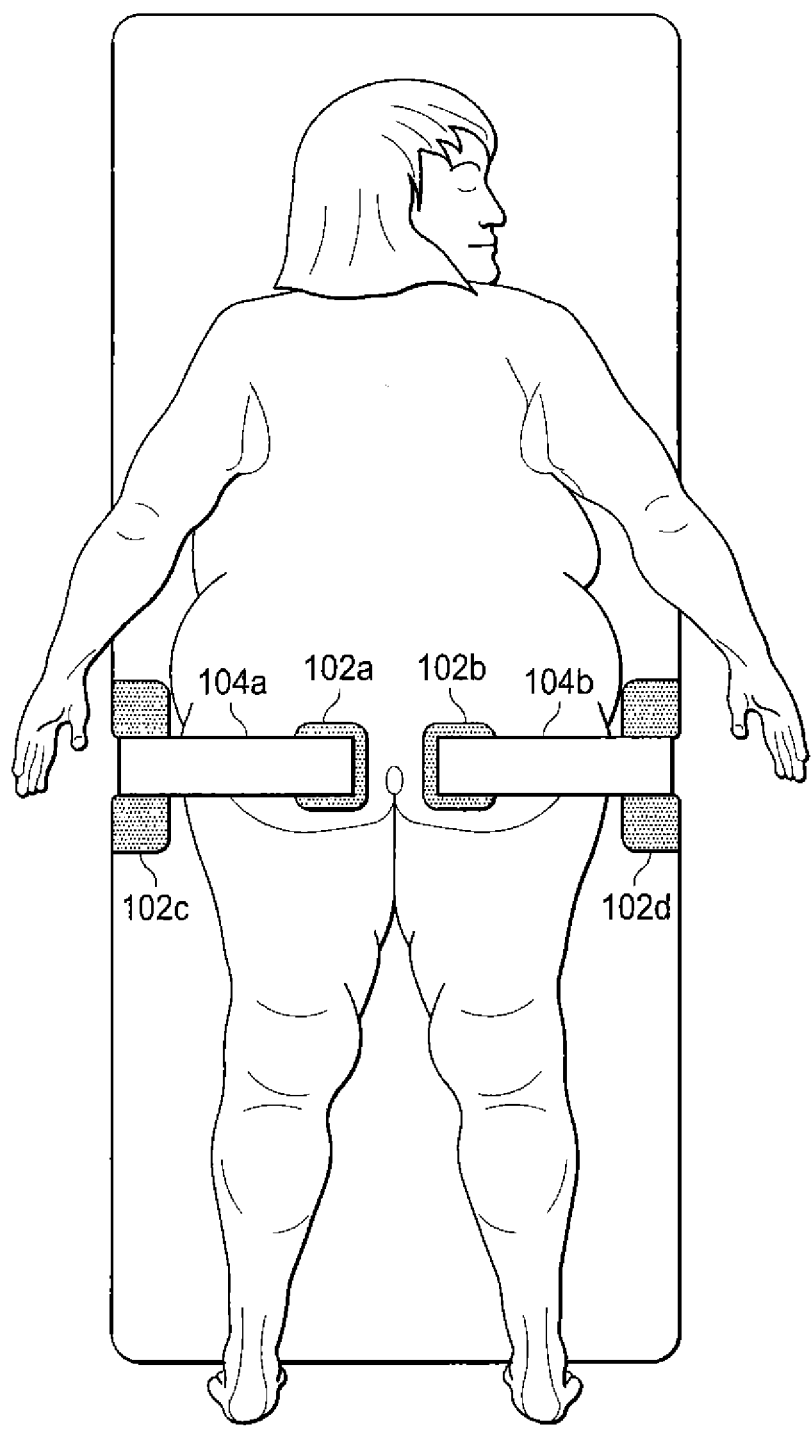
FIG. 7 is an illustration showing an exemplary application of the tissue retention system to maintain the buttocks of a patient in a displaced position.

FIG. 7 shows another alternative use of the tissue retention system. Here, a first anchor pad 102a is attached to a patient's right buttocks and a second anchor pad 102b is attached to the patient's left buttocks. Third and fourth anchor pads 102c, 102d are attached to support structure, such as the bed or table. Tension members 104a, 104b extend in opposing directions between the first and third anchor pads 102a, 102c and between the second and fourth anchor pads 102b, 102d to displace the buttocks and expose the rectum. This may provide better visualization during, for example, hemorrhoid surgery or repair of the anus, among other procedures.

Figure 8:
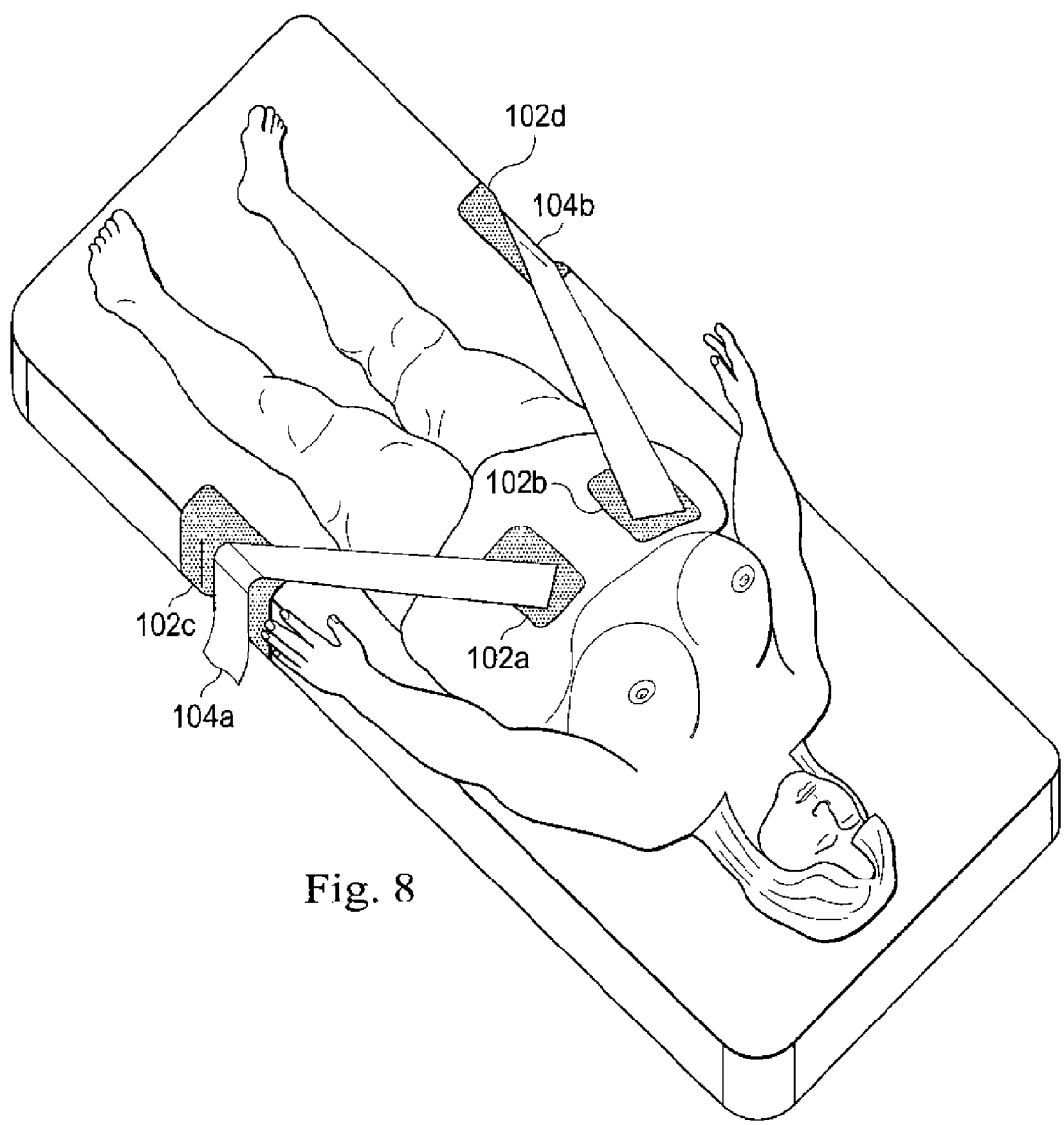
FIGS. 8-10 are illustrations showing an exemplary application of the tissue retention system to maintain adipose tissue of a patient in a displaced position.
Figure 9:
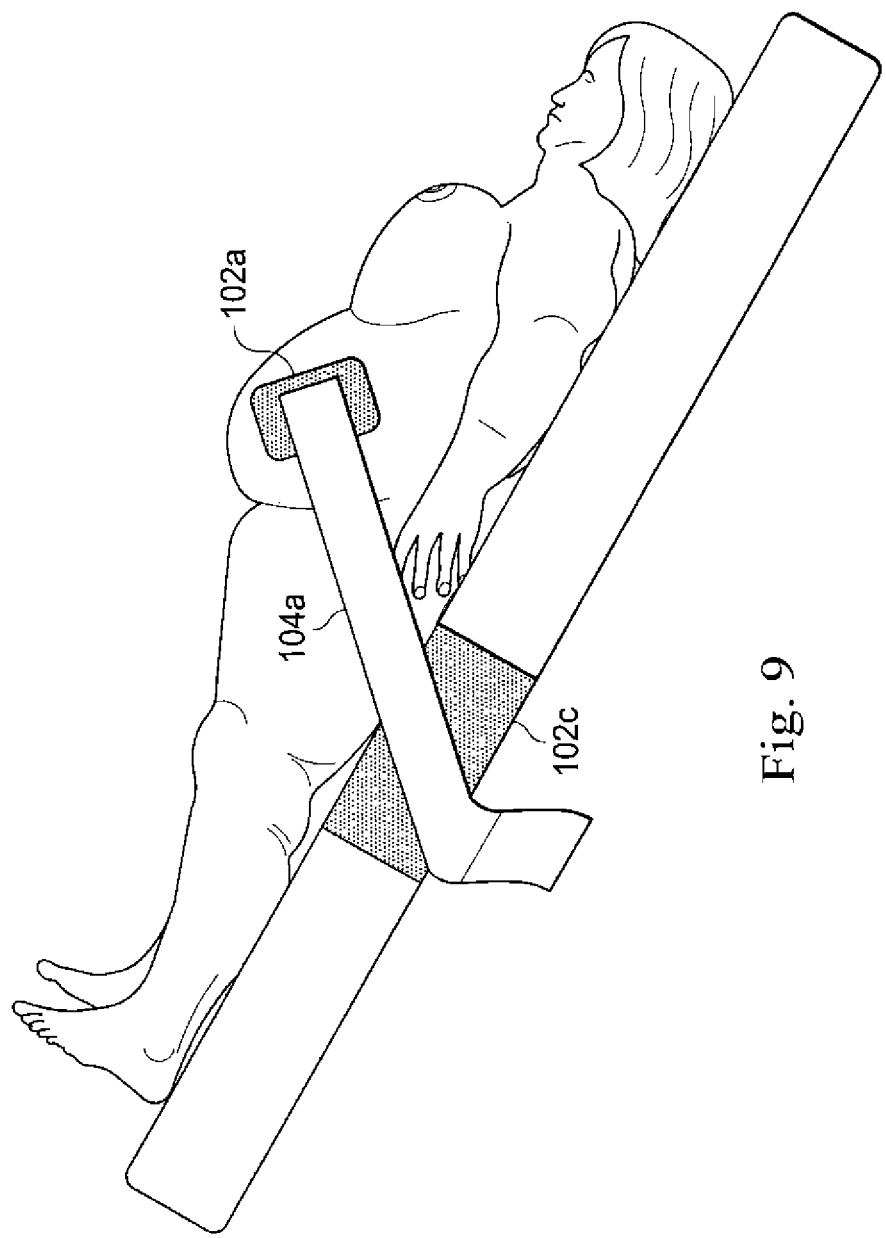
Figure 10:
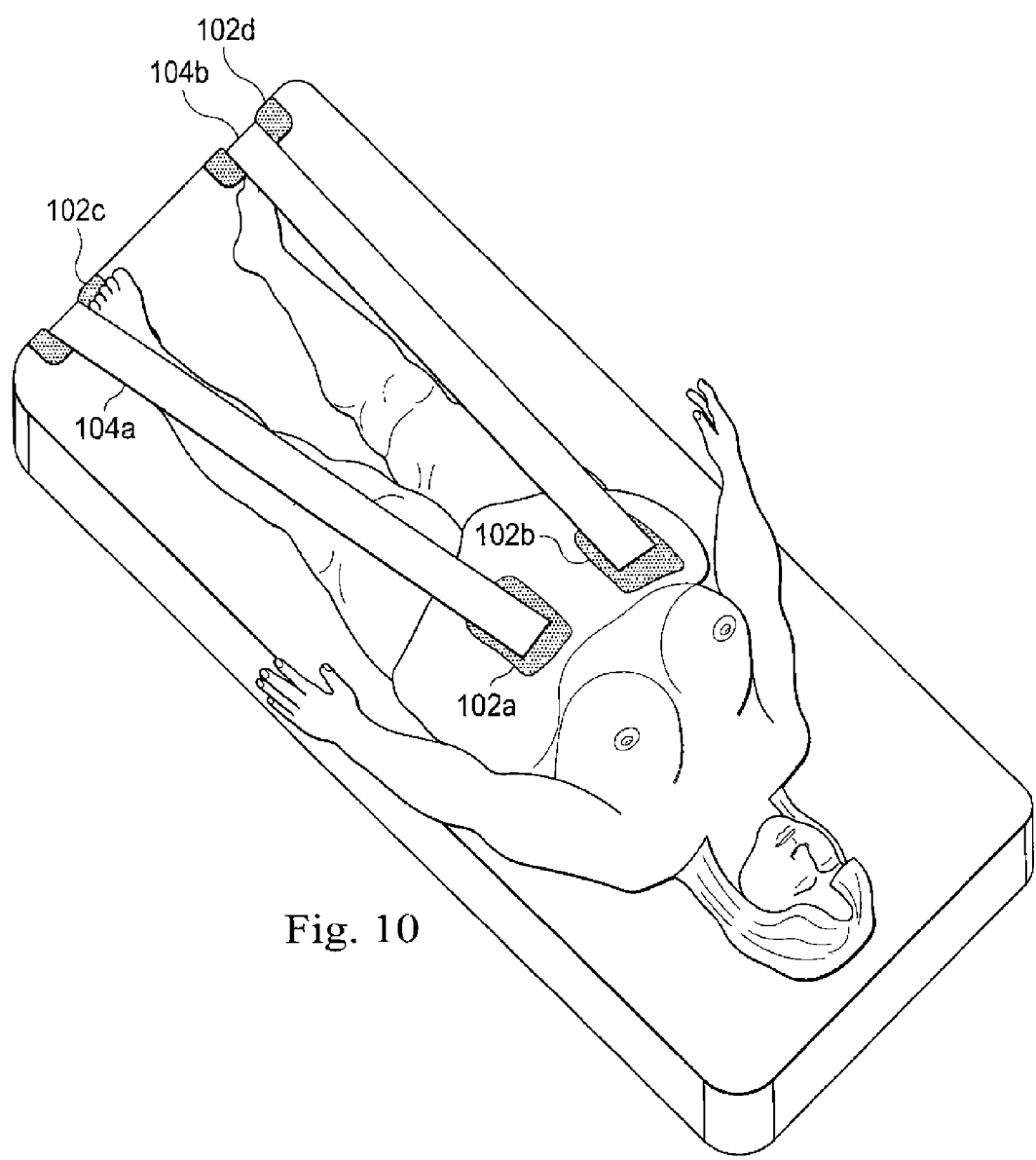

FIGS. 8-10 show additional alternative uses of the tissue retention system. In these embodiments, the patient is placed in a supine position as required by certain surgical procedures. In the examples shown, the patient's torso is elevated higher than the patient's head. In so doing however, the weight of the pannus, which on some obese patients may be more than one hundred pounds, may shift to at least partially lie on the patient's lungs, rendering breathing difficult or impossible.

The tissue retention system disclosed herein however, may be used to alleviate some of the weight on the lungs by maintaining the adipose tissue, such as the pannus, in its more natural location. FIGS. 8 and 9 show a first embodiment of such a method with FIG. 8 being a top view and FIG. 9 being a side of patient in the supine position. FIG. 10 shows an alternative embodiment.

Referring to FIGS. 8-10, first and second anchor pads 102a, 102b are attached to a patient's adipose tissue roll above the pannus. Third and fourth anchor pads 102c, 102d are attached to support structure, such as the bed or table. Tension members 104a, 104b extend in the direction of the patient's feet to displace or maintain the adipose tissue in a desired position. FIG. 9, because of its view, shows the tissue retention system 100 on only one side of the patient. It is contemplated that in some embodiments, the tissue retention system would include the additional anchor pads and tension members as shown in FIG. 8.

In FIGS. 8 and 9, the tension members 104a, 104b are attached to sides of the table and in FIG. 10, the tension members 104a, 104b are attached to an end of the table. Accordingly, the weight of the pannus is maintained in an area at least partially off the lungs permitting the patient to continue to breathe more easily.

It is contemplated that the tissue retention system disclosed herein may be robust enough to maintain displaced tissue that applies loading on the retention system of, for example, more than 20 lbs. In some aspects, the system is robust enough to maintain displaced tissue weighing more than 25 lbs, 30 lbs, 40 lbs, 50 lbs, 75 lbs, 100 lbs, and 150 lbs. Other amounts, both larger and smaller are also contemplated.

It is noted that the tissue retention system may be used to simultaneously displace adipose tissue from different parts of the body. For example, for a femoral catheterization procedure, medical personnel may use the tissue retention system to displace the pannus and the thigh in the manners discussed above. Once the tissue is maintained in a displaced position, the femoral region may be cleansed and the procedures performed, such as introducing a needle through the cleansed portion of the femoral region. In addition, it is contemplated that when multiple anchor pads are used, they may be different sizes depending upon their purpose.

Figure 11:
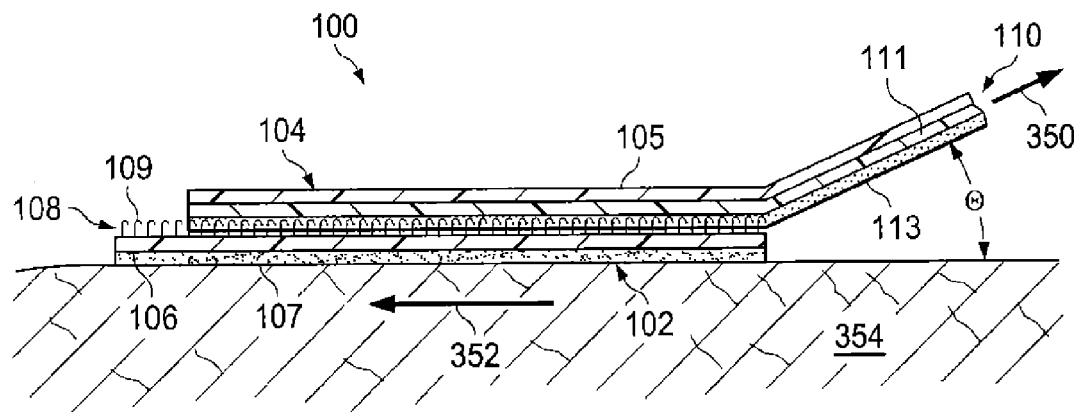
FIG. 11 is an illustration showing exemplary directional loading of components of the tissue retention system.

FIG. 11 shows the direction of exemplary loading of the tension member 104 relative to the position of the anchor pad 102 when maintaining adipose tissue in a displaced position. Here, the tension member 104 is shown under a tension load identified by the force arrow 350. A counteracting force identified by a force arrow 352 acts between the anchor pad 102 and adipose tissue on a patient, represented by the reference numeral 354. We note that the force arrow 352 may include a transverse component (not shown) that counters the tension load acting on the tension member 104. Here, the tension member 104 is shown loaded at an angle θ relative to the attachment surface 108 of the anchor pad 102. In use, loading applied from the tension member 104, through the anchor pad 102 and skin, to the tissue 354 is at an angle less than normal to the attachment surface 108. Accordingly, the range of loading angles θ may fall within the range of about −75 to 75 degrees. A force applied at an angle θ of about 90 degrees or greater would separate the fastening surfaces of the tension member 104 and anchor pad 102. In some embodiments, the loading occurs at an angle θ within the range of about 60 to 60 degrees relative to the fastening surface of the anchor pad. In other embodiments, the loading occurs at an angle θ within the range of about −45 to 45 degrees relative to the fastening surface of the anchor pad. Other angles also are contemplated. In some embodiments, when the anchor pad 102 is placed on a curved surface, the tension member 104 may apply a tension load at an angle θ within the range of about −60 to 60 degrees relative to a line tangent to the fastening surface of the anchor pad at the location where the anchor pad 102 and the tension member 104 separate.

While the examples set forth herein primarily describe attaching the anchor pads directly to the skin, in some alternatives, the anchor pads attach to surgical drapes over an incision. Accordingly, in these instances, the anchor pads may not attach directly to the skin, but attach to the surgical drapes adhered to the skin.

Figure 12:
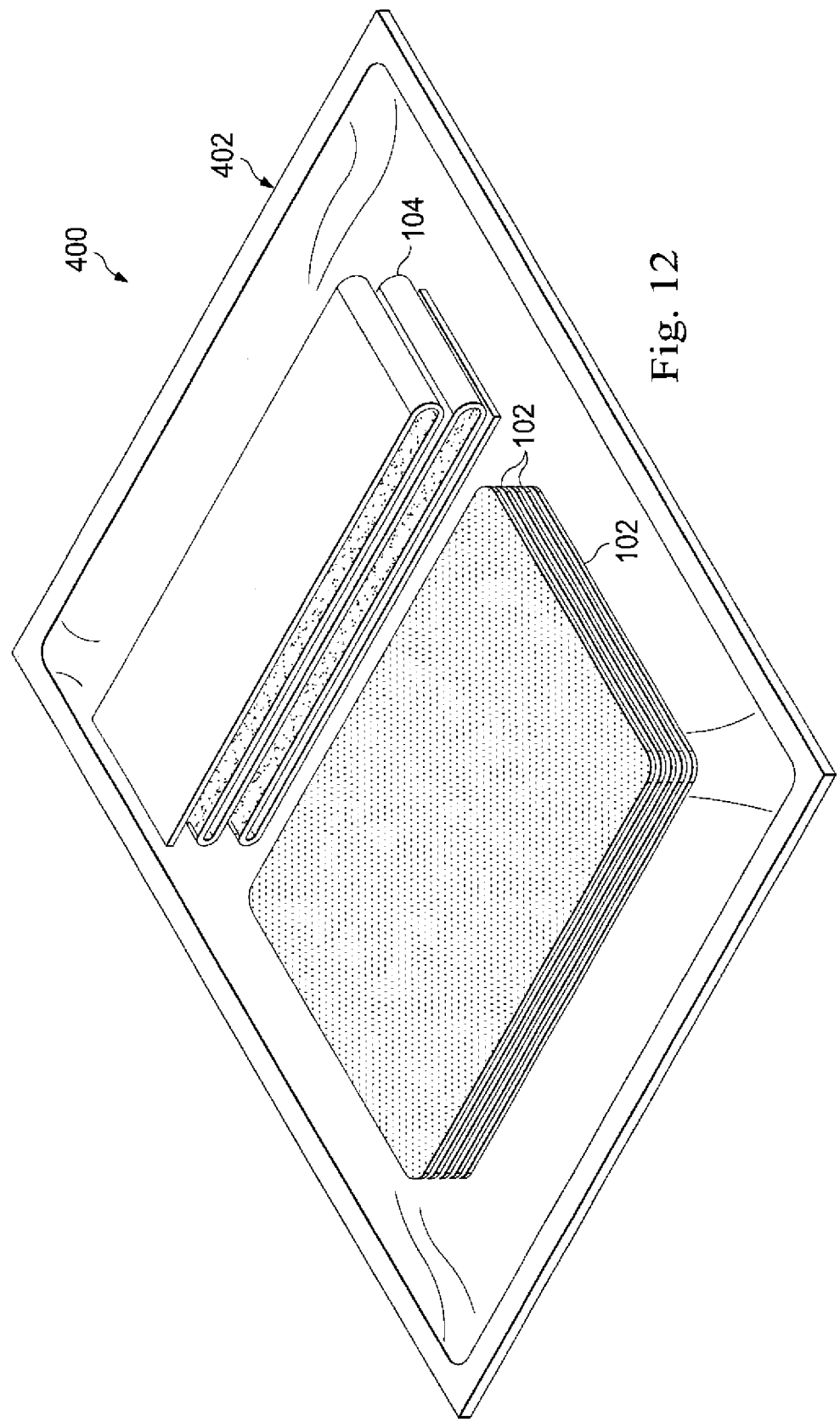
FIG. 12 is an illustration showing an exemplary kit having components of the tissue retention system.

In addition, the tissue retention system may be a part of a kit. One example of a kit, referenced herein as 400 is shown in FIG. 12. With reference to FIG. 12, the kit 400 is disposed in an envelope 402 and includes a plurality of pads 102 and a single tension member 104 that may be cut to a desired length during use. In some examples, four pads 102 may be provided with a single tension member 104. In other examples, four pads 102 may be provided with two or more tension members 104. In yet other embodiments, the kit includes two anchor pads 102 and one tension member 104. In some embodiments, a second envelope (not shown) may be provided within the envelope 402 and may contain therein the anchor pads 102. This keeps the tension member and pads from attaching to each other during storage or shipping and provides easier access to an attending health care provider. Other configurations of the above are also contemplated.

In some embodiments, the kit may be assembled for specific surgical procedures. For example, a child birthing kit may include one or more anchor pads, one or more tension members, a cotton tip applicator, bulb syringe, pads, gauze, suction tubing, cord clamp, and a Foley catheter. It also may include a drape, table cover, gowns, basins, bowls, laps, absorbent towels, disposal bags, mayo stand cover, Bovie, sterile towels, light handle covers, labels, marking pen, and drapes/pouch, among other items. The kit also may include these following items that may be used during the procedure: a drape, table cover, gowns, 2 basins, laps, 1 disposal bag, needle counter, 1 six inch cotton tip applicator, tray organizer, 1 bulb syringe, 1 mayo stand cover, 1 CSR, wrap×2, Bovie (cauterizing unit), 1 pitcher (1200 ml), sterile towels, 2 pads, 1 gauze 18"×18", 2 light handle covers, 4×4 raytex-10, 1 absorbent towel, 1 blue bowl, suction tubing, labels, 1-CSR poly-back, 2 #20 blades, cord clamp, marking pen, suction equipment, drapes/pouch, Foley catheter. In also may include the physician's preference for sutures, dressing, staples, JP drains. A discussion of an exemplary method and/or additional items that may be included in the kit is provided in U.S. Pat. Nos. 4,880,418, 5,676,672, and 6,102,924, all incorporated herein in their entirety by reference.

In another example, a femoral catheterization kit may include one or more anchor pads, one or more tension members, a needle sized to puncture the patient's skin and enter the femoral artery, and a flexible hollow tube such as a catheter for threading through the femoral artery. A discussion of an exemplary method and additional items that may be included in the kit is provided in U.S. Pat. No. 4,355,026, incorporated herein in its entirety by reference.

In yet another example, a hysterectomy kit may include one or more anchor pads, one or more tension members, pads, gauze, cotton tip applicator, suction tubing, and a Foley catheter. It also may include a drape, table cover, a gown, a basin, a bowl, a lap, absorbent towels, disposal bags, mayo stand cover, Bovie, sterile towels, light handle covers, labels, marking pen, drapes/pouch. The kit also may include these following items that may be used during the procedure: a drape, table cover, gowns, 1 mayo stand cover, 2 light handle covers, suction equipment, irrigation, Bovie (cauterizing unit), laps, 1 disposal bag, sponges, absorbent towels. Graspers & dissectors: atraumatic graspers, soft bowel clamps, Maryland dissectors, scissors, needle holders, bipolar forceps and cord, endoloop, tissue morecellator for large uterus. Vaginal instrument table: single tooth tenaculum, Alis graspers, dilators, uterine manipulator, Cohen cannula, speculum, Foley catheter. If doing laparoscopic hysterectomy, the kit also may include 10 mm, 0 degree laparoscope 3 sizes (2-3 mm, 5 mm, 10 mm), and trocars. It may also include the physician preference for suture, dressing, staples. Other kits and uses also are contemplated.

While providing many advantages over known systems, the tissue retention system disclosed herein is particularly useful on obese patients because it may be effectively used without wrapping around a portion of the patient. For example, it may be entirely applied and used without lifting of limbs, the head, the torso, or legs. It can be applied and used entirely from one side of the patient, such as the patient's front side or the patient's back side.

Other advantages and benefit may include one or more of the following:

allows caretaker to move flesh without breaking sterile field. After the pannus has been scrubbed and sterilized, it is not preferable to have nurses with their hands on the patient's Pannus. There is a greater possibility of contaminating the sterile field. When the anchor pads are placed on the patient's Pannus and the ends of the tension members are attached to pads anchored on the table, the caregiver may adjust and move the pannus by adjusting the tension members (without actually touching the patient);

frees the hands of the anesthesiologist or nurse (oftentimes, these individuals assist the physician in holding up the pannus of obese patients);

unlike tape and adhesives, this method of securing and/or moving flesh applies adhesive only to the Pannus, while the tension member does not directly adhere to the patient's skin. With tape, the entire contact area has adhesive. This is problematic because a) it is a time consuming process to wrap tape around someone's Pannus and secure it to their shoulders or around the patient's neck, and b) when tape is used, the skin underneath all the tape (not just the tape on the Pannus) now has adhesive all over it (i.e. tape around the shoulders, neck, and sides);

eliminates the need for Benzoin spray as an adhesive;

quickly applied and removed;

unlike narrow tape, the anchor pads distribute loads across a larger surface area (which is better on the patient's skin);

allows user to "reposition" anatomy; and latex free and residue free (when you remove the pads from the patient's skin, tape residue may be not left on the skin). It is designed to maintain maximum sheer loads while supporting, retaining, or moving large masses of tissue.

In addition to being useful for the procedures discussed above, the tissue retention system also may be used in Bariatric procedures. Such procedures may include the steps of, for example, adhering a first anchor pad to the patient's skin adjacent the adipose tissue and adhering a second anchor pad at a second supporting location, such as for example, on the patient or on the surgical table. The tension member may be selectively fastened in tension to the two anchor pads in a manner that the adipose tissue is disposed in a displaced position. For example, it may be used to maintain tissue in a displaced position in procedures such as: Laparoscopic Roux-En-Y Gastric Bypass, Laparoscopic Vertical Banded Gastroplasty, Laparoscopic Adjustable Banding, Laparoscopic Bileopancreatic Diversion, Laparoscopic BPD & Duodenal Switch, Standard Roux-En-Y Gastric Bypass, Distal Roux-En-Y Gastric Bypass, Other Gastric Bypass Procedures, Vertical Banded Gastroplasty, Silastic Ring Gastroplasty, Gastric Banding, Banded Gastric Bypass, and Other Gastric Restriction, Biliopancreatic Diversion, among other Bariatric procedures. It may be used with additional procedures, including, for example, Laparoscopic Adjustable Gastric Banding Procedure or Lap-Band procedures. During set-up, during the procedure, or afterward, the tension member may be optionally removed from one or both of the anchor pads and adjusted in order to displace the adipose tissue to a different position. After the procedure, the tension member may be removed from the anchor pads and the anchor pads may be removed from the patient's skin.

Applicants note that the procedures disclosed herein are merely exemplary and that the systems and method disclosed herein may be utilized for numerous other medical processes and procedures. Although several selected embodiments have been illustrated and described in detail, it will be understood that they are exemplary, and that a variety of substitutions and alterations are possible without departing from the spirit and scope of the present invention, as defined by the following claims.

We claim:

1. A method of maintaining adipose tissue on a patient in a displaced position during a medical procedure to provide access to a body portion of the patient with a tissue retention system, the method comprising:
   adhesively adhering directly to a patient's skin adjacent the adipose tissue an adhesive surface of an anchor pad, the anchor pad having a pad length and a pad width, the anchor pad having an opposing first selective attachment surface facing away from the adhesive surface, the first selective attachment surface including a hook portion of a hook and loop fastener;
   attaching a first portion of a tension member having a second selective attachment surface to the first selective attachment surface of the anchor pad, the second selective attachment surface including a loop portion of the hook and loop fastener;
   displacing adipose tissue from a natural position to a displaced position; and
   maintaining the adipose tissue in the displaced position with the tension member.

2. The method of claim 1, wherein maintaining the adipose tissue in the displaced position with the tension member includes loading the tension member in tension such that the tension member applies a loading force on the anchor pad at an angle less than 45 degrees measured from the first selective attachment surface of the anchor pad.

3. The method of claim 2, including laying the patient in a prone position, and wherein the steps of adhering, displacing, attaching, and maintaining are performed without lifting the limbs, the torso, or the head of the patient.

4. The method of claim 3, further including:
   adhesively adhering a second anchor pad directly on the patient; and
   attaching a second portion of the tension member to the second anchor pad.

5. The method of claim 4, wherein adhesively adhering a second anchor pad directly on the patient includes adhering the second anchor pad on or about the patient's shoulder.

6. The method of claim 1, further including:
   adhesively adhering a second anchor pad to a fixed surface; and
   attaching a second portion of the tension member to the second anchor pad.

7. The method of claim 6, wherein adhesively adhering a second anchor pad to a fixed surface includes adhering the second anchor pad to a surgical table or bed.

8. The method of claim 1, wherein pad width is greater than the pad length and wherein adhesively adhering includes orienting the anchor pad so that the width is transverse to the desired direction of tissue displacement.

9. The method of claim 1, wherein the stop of attaching a first portion of a tension member occurs prior to displacing adipose tissue.

10. The method of claim 1, wherein the patient's skin adjacent the adipose tissue includes the abdomen, and wherein adhesively adhering includes placing the anchor pad on the abdomen of the patient.

11. The method of claim 1, wherein the patient's skin adjacent the adipose tissue includes the thigh, and wherein adhesively adhering includes placing the anchor pad on the thigh of the patient.

12. The method of claim 1, wherein the patient's skin adjacent the adipose tissue includes the breast, and wherein adhesively adhering includes placing the anchor pad on the breast of the patient.

13. The method of claim 1, wherein the patient's skin adjacent the adipose tissue includes the buttocks, and wherein adhesively adhering includes placing a first anchor pad on the right buttocks of the patient and placing a second anchor pad on the left buttocks of the patient.

14. A method of maintaining a pannus on a patient in a displaced position during a medical procedure to provide access to a body region of the patient with a tissue retention system, the method comprising:
   adhesively adhering directly to a patient's abdomen an adhesive surface of a first anchor pad, the first anchor pad having a pad length and a pad width, the first anchor pad having an opposing first selective attachment surface facing away from the adhesive surface;
   adhesively adhering a second anchor pad at an anchoring location spaced from the first anchor pad;
   attaching a first portion of a tension member having a second selective attachment surface to the first selective attachment surface of the anchor pad without adhesively adhering the tension member directly to the patient's skin;
   displacing adipose tissue on the abdomen from a natural position to a displaced position;
   attaching a second portion of the tension member to the second anchor pad so that the tension member is in tension between the first and the second anchor pads; and
   maintaining the adipose tissue in the displaced position with the tension member.

15. The method of claim 14, wherein adhesively adhering includes placing the anchor pad on the skin that is under the fold of the lower abdomen of the patient.

16. The method of claim 15, wherein adhesively adhering a second anchor pad to an anchoring location includes adhesively adhering to one of an operating table and the patient's skin.

17. The method of claim 14, wherein adhesively adhering a second anchor pad to a surface includes adhesively adhering to the second anchor pad to a shoulder of the patient.

18. The method of claim 14, wherein displacing adipose tissue from a natural position to a displaced position is performed after attaching the first portion of the tension member to the first selective attachment surface of the anchor pad, and includes pulling on the tension member to displace the adipose tissue.

19. The method of claim 14, comprising:
   adjusting the displaced adipose tissue, including:

detaching the support member from one of the first and second anchor pads;
further displacing the adipose tissue; and
reattaching the tension member to the one of the first and second anchor pads.

20. A method of maintaining adipose tissue on a patient in a displaced position during a medical procedure to provide access to a body portion of the patient with a tissue retention system, the method comprising:
adhesively adhering directly to a patient's skin an adhesive surface of an anchor pad, the anchor pad having an opposing first selective attachment surface facing away from the adhesive surface;
attaching a first portion of a tension member having a second selective attachment surface to the first selective attachment surface of the anchor pad without adhesively adhering the tension member directly to the patient's skin;
displacing adipose tissue from a natural position to a displaced position; and
maintaining the adipose tissue in the displaced position with the tension member.

* * * * *